US012765811B2

(12) United States Patent
Kane et al.

(10) Patent No.: US 12,765,811 B2
(45) Date of Patent: Oct. 20, 2026

(54) STRUCTURAL DIFFUSION MEMBRANES FOR CHEMICAL SENSORS

(71) Applicant: Cardiac Pacemakers, Inc., St. Paul, MN (US)

(72) Inventors: Michael J. Kane, St. Paul, MN (US); Yingbo Li, Woodbury, MN (US); Jack Gordon, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 305 days.

(21) Appl. No.: 18/582,747

(22) Filed: Feb. 21, 2024

(65) Prior Publication Data

US 2024/0268718 A1 Aug. 15, 2024

Related U.S. Application Data

(63) Continuation of application No. 16/130,638, filed on Sep. 13, 2018, now abandoned.

(30) Foreign Application Priority Data

Oct. 31, 2017 (CN) ........................ 201711052948.1

(51) Int. Cl.

*A61B 5/145* (2006.01)
*A61B 5/00* (2006.01)
(Continued)

(52) U.S. Cl.

CPC ........ *A61B 5/14546* (2013.01); *A61B 5/1451* (2013.01); *A61B 5/1455* (2013.01);
(Continued)

(58) Field of Classification Search

CPC ... A61B 5/0031; A61B 5/686; A61B 5/14507; A61B 5/14546; A61B 5/1459; A61B 5/1473
See application file for complete search history.

(56) References Cited

U.S. PATENT DOCUMENTS 556,421 A 3/1896 Judge
4,181,863 A 1/1980 Parker
(Continued)

FOREIGN PATENT DOCUMENTS

CN 1956678 5/2007
CN 102165070 8/2011
(Continued)

OTHER PUBLICATIONS

"Non-Final Office Action," for U.S. Appl. No. 17/510,903 mailed May 19, 2025 (20 pages).
(Continued)

*Primary Examiner* — Puya Agahi
(74) *Attorney, Agent, or Firm* — Pauly, DeVries Smith & Deffner LLC

(57) ABSTRACT

Embodiments herein relate to implantable chemical sensors for detecting a physiological analyte and medical devices including the same. In an embodiment, an implantable medical device is included. The implantable medical device can include a chemical sensor configured to detect an ion concentration in a bodily fluid. The chemical sensor can include a sensing element. The sensing element can include an outer barrier layer forming a top, a bottom, and opposed sides of the sensing element and a structural reinforcing element contacting the outer barrier layer. The top of the outer barrier layer of the sensing element can include a polymeric matrix permeable to analytes.

12 Claims, 6 Drawing Sheets

(51) Int. Cl.
*A61B 5/1455* (2006.01)
*A61B 5/1459* (2006.01)
*A61B 5/1473* (2006.01)

(52) U.S. Cl.
CPC .......... *A61B 5/1459* (2013.01); *A61B 5/1473* (2013.01); *A61B 5/14735* (2013.01); *A61B 5/0059* (2013.01); *A61B 5/0075* (2013.01); *A61B 5/145* (2013.01); *A61B 2562/162* (2013.01)

(56) References Cited

U.S. PATENT DOCUMENTS

| | | | |
|---|---|---|---|
| 4,200,110 | A | 4/1980 | Peterson et al. |
| 4,321,057 | A | 3/1982 | Buckles |
| 4,344,438 | A | 8/1982 | Schultz et al. |
| 4,399,099 | A | 8/1983 | Buckles |
| 4,680,268 | A | 7/1987 | Clark |
| 4,704,029 | A | 11/1987 | Van Heuvelen |
| 4,721,677 | A | 1/1988 | Clark |
| 4,750,494 | A | 6/1988 | King |
| 4,750,495 | A | 6/1988 | Moore et al. |
| 4,890,621 | A | 1/1990 | Hakky |
| 4,903,701 | A | 2/1990 | Moore |
| 4,981,779 | A | 1/1991 | Wagner |
| 5,001,054 | A | 3/1991 | Wagner |
| 5,040,533 | A | 8/1991 | Fearnot |
| 5,090,326 | A | 2/1992 | Altenau et al. |
| 5,209,231 | A | 5/1993 | Cote et al. |
| 5,267,151 | A | 11/1993 | Ham et al. |
| 5,275,171 | A | 1/1994 | Barcel |
| 5,312,439 | A | 5/1994 | Loeb |
| 5,312,454 | A | 5/1994 | Roline et al. |
| 5,330,718 | A | 7/1994 | Hui et al. |
| 5,333,609 | A | 8/1994 | Bedingham et al. |
| 5,342,406 | A | 8/1994 | Thompson |
| 5,342,789 | A | 8/1994 | Chick et al. |
| 5,355,880 | A | 10/1994 | Thomas et al. |
| 5,378,432 | A | 1/1995 | Bankert et al. |
| 5,419,329 | A | 5/1995 | Smith et al. |
| 5,457,535 | A | 10/1995 | Schmidtke et al. |
| 5,476,434 | A | 12/1995 | Kalb et al. |
| 5,553,616 | A | 9/1996 | Ham et al. |
| 5,556,421 | A | 9/1996 | Prutchi et al. |
| 5,560,356 | A | 10/1996 | Peyman |
| 5,605,152 | A | 2/1997 | Slate et al. |
| 5,607,644 | A | 3/1997 | Olstein et al. |
| 5,660,163 | A | 8/1997 | Schulman et al. |
| 5,728,281 | A | 3/1998 | Holmstrom et al. |
| 5,730,125 | A | 3/1998 | Prutchi et al. |
| 5,741,211 | A | 4/1998 | Renirie et al. |
| 5,797,898 | A | 8/1998 | Santini et al. |
| 5,830,138 | A | 11/1998 | Wilson |
| 5,833,603 | A | 11/1998 | Kovacs et al. |
| 5,854,078 | A | 12/1998 | Asher |
| 5,871,442 | A | 2/1999 | Madarasz et al. |
| 5,902,326 | A | 5/1999 | Lessar et al. |
| 5,958,782 | A | 9/1999 | Bentsen et al. |
| 5,995,860 | A | 11/1999 | Sun et al. |
| 6,002,954 | A | 12/1999 | Van Antwerp et al. |
| 6,011,984 | A | 1/2000 | Van Antwerp et al. |
| 6,040,194 | A | 3/2000 | Chick et al. |
| 6,049,727 | A | 4/2000 | Crothall |
| 6,070,093 | A | 5/2000 | Oosta et al. |
| 6,097,139 | A | 8/2000 | Tuck et al. |
| 6,122,536 | A | 9/2000 | Sun et al. |
| 6,123,861 | A | 9/2000 | Santini et al. |
| 6,125,290 | A | 9/2000 | Miesel |
| 6,125,291 | A | 9/2000 | Miesel et al. |
| 6,134,459 | A | 10/2000 | Roberts et al. |
| 6,144,866 | A | 11/2000 | Miesel et al. |
| 6,163,714 | A | 12/2000 | Stanley et al. |
| 6,175,642 | B1 | 1/2001 | Gobbi et al. |
| 6,187,599 | B1 | 2/2001 | Asher et al. |
| 6,216,022 | B1 | 4/2001 | Tyrrell et al. |
| 6,219,137 | B1 | 4/2001 | Vo-Dinh |
| 6,232,130 | B1 | 5/2001 | Wolf |
| 6,236,870 | B1 | 5/2001 | Madarasz et al. |
| 6,256,522 | B1 | 7/2001 | Schultz |
| 6,267,724 | B1 | 7/2001 | Taylor et al. |
| 6,268,161 | B1 | 7/2001 | Han et al. |
| 6,277,627 | B1 | 8/2001 | Hellinga |
| 6,304,766 | B1 | 10/2001 | Colvin, Jr. |
| 6,330,464 | B1 | 12/2001 | Colvin et al. |
| 6,343,223 | B1 | 1/2002 | Chin et al. |
| 6,344,340 | B1 | 2/2002 | Dibner et al. |
| 6,368,274 | B1 | 4/2002 | Van Antwerp et al. |
| 6,383,767 | B1 | 5/2002 | Polak |
| 6,438,397 | B1 | 8/2002 | Bosquet et al. |
| 6,442,409 | B1 | 8/2002 | Peyman |
| 6,454,710 | B1 | 9/2002 | Ballerstadt et al. |
| 6,466,821 | B1 | 10/2002 | Pianca et al. |
| 6,491,639 | B1 | 12/2002 | Turcott |
| 6,491,666 | B1 | 12/2002 | Santini et al. |
| 6,505,059 | B1 | 1/2003 | Kollias et al. |
| 6,521,446 | B2 | 2/2003 | Hellinga |
| 6,527,762 | B1 | 3/2003 | Santini et al. |
| 6,544,800 | B2 | 4/2003 | Asher |
| 6,551,838 | B2 | 4/2003 | Santini et al. |
| 6,579,690 | B1 | 6/2003 | Bonnecaze et al. |
| 6,594,092 | B2 | 7/2003 | Von et al. |
| 6,594,510 | B2 | 7/2003 | Madarasz et al. |
| 6,602,521 | B1 | 8/2003 | Ting et al. |
| 6,625,479 | B1 | 9/2003 | Weber et al. |
| 6,666,821 | B2 | 12/2003 | Keimel et al. |
| 6,671,527 | B2 | 12/2003 | Petersson et al. |
| 6,673,596 | B1 | 1/2004 | Sayler et al. |
| 6,682,938 | B1 | 1/2004 | Satcher, Jr. et al. |
| 6,694,158 | B2 | 2/2004 | Polak |
| 6,711,423 | B2 | 3/2004 | Colvin |
| 6,731,976 | B2 | 5/2004 | Penn et al. |
| RE38,525 | E | 6/2004 | Stanley et al. |
| 6,766,183 | B2 | 7/2004 | Walsh |
| 6,771,993 | B2 | 8/2004 | Rule et al. |
| 6,800,451 | B2 | 10/2004 | Daniloff et al. |
| 6,804,544 | B2 | 10/2004 | Van Antwerp et al. |
| 6,814,490 | B1 | 11/2004 | Suhm et al. |
| 6,815,162 | B2 | 11/2004 | Boukherroub et al. |
| 6,835,553 | B2 | 12/2004 | Han et al. |
| 6,855,556 | B2 | 2/2005 | Amiss et al. |
| 6,875,208 | B2 | 4/2005 | Santini et al. |
| 6,885,881 | B2 | 4/2005 | Leonhardt |
| 6,885,883 | B2 | 4/2005 | Parris et al. |
| 6,893,545 | B2 | 5/2005 | Gotoh et al. |
| 6,912,078 | B2 | 6/2005 | Kudrle et al. |
| 6,918,873 | B1 | 7/2005 | Millar et al. |
| 6,928,325 | B2 | 8/2005 | Zhu et al. |
| 6,937,900 | B1 | 8/2005 | Pianca et al. |
| 6,944,488 | B2 | 9/2005 | Roberts |
| 6,952,603 | B2 | 10/2005 | Gerber et al. |
| 6,957,094 | B2 | 10/2005 | Chance et al. |
| 6,976,982 | B2 | 12/2005 | Santini et al. |
| 6,978,182 | B2 | 12/2005 | Mazar et al. |
| 7,016,714 | B2 | 3/2006 | Colvin, Jr. et al. |
| 7,039,446 | B2 | 5/2006 | Ruchti et al. |
| 7,070,590 | B1 | 7/2006 | Santini et al. |
| 7,107,086 | B2 | 9/2006 | Reihl et al. |
| 7,133,710 | B2 | 11/2006 | Acosta et al. |
| 7,134,999 | B2 | 11/2006 | Brauker et al. |
| 7,144,474 | B1 | 12/2006 | Hansen et al. |
| 7,157,723 | B2 | 1/2007 | Colvin et al. |
| 7,164,948 | B2 | 1/2007 | Struble et al. |
| 7,166,871 | B2 | 1/2007 | Erchak |
| 7,174,212 | B1 | 2/2007 | Klehn et al. |
| 7,181,096 | B2 | 2/2007 | Matsumoto et al. |
| 7,225,024 | B2 | 5/2007 | Zhu et al. |
| 7,236,821 | B2 | 6/2007 | Cates et al. |
| 7,410,616 | B2 | 8/2008 | Santini et al. |
| 7,447,533 | B1 | 11/2008 | Fang et al. |
| 7,449,246 | B2 | 11/2008 | Kim et al. |
| 7,450,980 | B2 | 11/2008 | Kawanishi |
| 7,471,290 | B2 | 12/2008 | Wang et al. |
| 7,577,470 | B2 | 8/2009 | Shah et al. |
| 7,632,234 | B2 | 12/2009 | Manda et al. |

(56) References Cited

U.S. PATENT DOCUMENTS

| | | | |
|---|---|---|---|
| 7,633,356 | B2 | 12/2009 | Hamet et al. |
| 7,686,762 | B1 | 3/2010 | Najafi et al. |
| 7,761,130 | B2 | 7/2010 | Simpson et al. |
| 7,805,174 | B2 | 9/2010 | Carpenter et al. |
| 7,809,441 | B2 | 10/2010 | Kane et al. |
| 7,829,147 | B2 | 11/2010 | Aitken et al. |
| 7,890,171 | B2 | 2/2011 | Zhu et al. |
| 7,894,884 | B2 | 2/2011 | Song et al. |
| 7,935,499 | B2 | 5/2011 | Dunn et al. |
| 8,126,554 | B2 | 2/2012 | Kane et al. |
| 8,131,364 | B2 | 3/2012 | Zhu et al. |
| 8,141,489 | B2 | 3/2012 | Belanger et al. |
| 8,160,670 | B2 | 4/2012 | Ouyang et al. |
| 8,165,840 | B2 | 4/2012 | Hatlestad et al. |
| 8,257,067 | B2 | 9/2012 | Fukui et al. |
| 8,290,592 | B2 | 10/2012 | Michael et al. |
| 8,303,511 | B2 | 11/2012 | Eigler et al. |
| 8,378,453 | B2 | 2/2013 | Fedorov et al. |
| 8,414,489 | B2 | 4/2013 | Shah et al. |
| 8,435,604 | B2 | 5/2013 | Aitken et al. |
| 8,527,067 | B2 | 9/2013 | De Kock et al. |
| 8,571,659 | B2 | 10/2013 | Kane et al. |
| 8,636,884 | B2 | 1/2014 | Feldman et al. |
| 8,710,625 | B2 | 4/2014 | Fedorov et al. |
| 8,765,060 | B2 | 7/2014 | Buhlmann et al. |
| 8,827,899 | B2 | 9/2014 | Farr et al. |
| 9,101,277 | B2 | 8/2015 | Doerr |
| 9,320,618 | B2 | 4/2016 | Schmitz et al. |
| 9,326,707 | B2 | 5/2016 | McGarraugh |
| 9,357,968 | B2 | 6/2016 | Hauer et al. |
| 9,399,076 | B2 | 7/2016 | Yu et al. |
| 9,693,714 | B2 | 7/2017 | Dehennis et al. |
| 10,154,918 | B2 | 12/2018 | Haselby et al. |
| 10,194,808 | B1 | 2/2019 | Thompson et al. |
| 10,543,371 | B2 | 1/2020 | Hunt et al. |
| 10,575,765 | B2 | 3/2020 | Brill |
| 10,667,745 | B2 | 6/2020 | Anker et al. |
| 10,716,500 | B2 | 7/2020 | Stahmann |
| 10,743,115 | B2 | 8/2020 | Frederiksen et al. |
| 10,952,621 | B2 | 3/2021 | Kane et al. |
| 11,089,983 | B2 | 8/2021 | Li et al. |
| 11,129,557 | B2 | 9/2021 | Li et al. |
| 11,439,304 | B2 | 9/2022 | Stahmann et al. |
| 11,571,151 | B2 | 2/2023 | Kane et al. |
| 12,004,853 | B2 | 6/2024 | Stahmann et al. |
| 12,551,145 | B2 | 2/2026 | Li et al. |
| 2002/0016535 | A1 | 2/2002 | Martin et al. |
| 2002/0026108 | A1 | 2/2002 | Colvin |
| 2002/0033260 | A1 | 3/2002 | Lungwitz et al. |
| 2002/0033454 | A1 | 3/2002 | Cheng et al. |
| 2002/0035317 | A1 | 3/2002 | Cheng et al. |
| 2002/0095075 | A1 | 7/2002 | Madarasz et al. |
| 2002/0127626 | A1 | 9/2002 | Daniloff et al. |
| 2002/0151812 | A1 | 10/2002 | Scheiner et al. |
| 2003/0100040 | A1 | 5/2003 | Bonnecaze et al. |
| 2003/0100822 | A1 | 5/2003 | Lew et al. |
| 2003/0114735 | A1 | 6/2003 | Silver et al. |
| 2003/0191376 | A1 | 10/2003 | Samuels et al. |
| 2003/0208113 | A1 | 11/2003 | Mault et al. |
| 2004/0023317 | A1 | 2/2004 | Motamedi et al. |
| 2004/0030365 | A1 | 2/2004 | Rubin |
| 2004/0059206 | A1 | 3/2004 | Braig et al. |
| 2004/0073100 | A1 | 4/2004 | Ballerstadt et al. |
| 2004/0087842 | A1 | 5/2004 | Lakowicz et al. |
| 2004/0100376 | A1 | 5/2004 | Lye et al. |
| 2004/0106953 | A1 | 6/2004 | Yomtov et al. |
| 2004/0132172 | A1 | 7/2004 | Cunningham et al. |
| 2004/0133079 | A1 | 7/2004 | Mazar et al. |
| 2004/0147034 | A1 | 7/2004 | Gore et al. |
| 2004/0161853 | A1 | 8/2004 | Yang et al. |
| 2004/0176669 | A1 | 9/2004 | Colvin, Jr. |
| 2004/0176672 | A1 | 9/2004 | Silver et al. |
| 2004/0180379 | A1 | 9/2004 | Van Duyne et al. |
| 2004/0180391 | A1 | 9/2004 | Gratzl et al. |
| 2004/0186359 | A1 | 9/2004 | Beaudoin et al. |
| 2004/0199062 | A1 | 10/2004 | Petersson et al. |
| 2004/0206916 | A1 | 10/2004 | Colvin, Jr. et al. |
| 2004/0215134 | A1 | 10/2004 | Soykan et al. |
| 2004/0249311 | A1 | 12/2004 | Haar et al. |
| 2004/0254438 | A1 | 12/2004 | Chuck et al. |
| 2004/0260162 | A1 | 12/2004 | Rohleder et al. |
| 2005/0027176 | A1 | 2/2005 | Xie |
| 2005/0033133 | A1 | 2/2005 | Kraft |
| 2005/0038329 | A1 | 2/2005 | Morris et al. |
| 2005/0042704 | A1 | 2/2005 | Alarcon et al. |
| 2005/0043894 | A1 | 2/2005 | Fernandez |
| 2005/0051427 | A1 | 3/2005 | Brauker et al. |
| 2005/0065464 | A1 | 3/2005 | Talbot et al. |
| 2005/0065556 | A1 | 3/2005 | Reghabi et al. |
| 2005/0069925 | A1 | 3/2005 | Ford et al. |
| 2005/0070768 | A1 | 3/2005 | Zhu et al. |
| 2005/0070770 | A1 | 3/2005 | Dirac et al. |
| 2005/0070771 | A1 | 3/2005 | Rule et al. |
| 2005/0096587 | A1 | 5/2005 | Santini et al. |
| 2005/0107677 | A1 | 5/2005 | Ward et al. |
| 2005/0113657 | A1 | 5/2005 | Alarcon et al. |
| 2005/0113658 | A1 | 5/2005 | Jacobson et al. |
| 2005/0130249 | A1 | 6/2005 | Parris et al. |
| 2005/0137481 | A1 | 6/2005 | Sheard et al. |
| 2005/0148832 | A1 | 7/2005 | Reghabi et al. |
| 2005/0149139 | A1 | 7/2005 | Plicchi et al. |
| 2005/0154272 | A1 | 7/2005 | Dirac et al. |
| 2005/0221276 | A1 | 10/2005 | Rozakis et al. |
| 2005/0221277 | A1 | 10/2005 | Kawanishi |
| 2005/0228226 | A1 | 10/2005 | Muckner |
| 2006/0025748 | A1 | 2/2006 | Ye |
| 2006/0076236 | A1 | 4/2006 | Shah et al. |
| 2006/0217771 | A1 | 9/2006 | Soykan et al. |
| 2006/0229694 | A1 | 10/2006 | Schulman et al. |
| 2006/0253043 | A1 | 11/2006 | Zhang et al. |
| 2006/0270923 | A1 | 11/2006 | Brauker et al. |
| 2007/0027495 | A1 | 2/2007 | Gerber |
| 2007/0118056 | A1 | 5/2007 | Wang et al. |
| 2007/0156194 | A1 | 7/2007 | Wang |
| 2007/0219628 | A1 | 9/2007 | Shanley et al. |
| 2007/0252713 | A1 | 11/2007 | Rondoni et al. |
| 2007/0270674 | A1 | 11/2007 | Kane et al. |
| 2007/0270675 | A1 | 11/2007 | Kane et al. |
| 2007/0275035 | A1 | 11/2007 | Herman et al. |
| 2008/0033260 | A1 | 2/2008 | Sheppard et al. |
| 2008/0046080 | A1 | 2/2008 | Vanden et al. |
| 2008/0077190 | A1 | 3/2008 | Kane |
| 2008/0082001 | A1 | 4/2008 | Hatlestad et al. |
| 2008/0086177 | A1 | 4/2008 | Min et al. |
| 2008/0152283 | A1 | 6/2008 | Nielsen et al. |
| 2008/0293997 | A1 | 11/2008 | Buhlmann et al. |
| 2008/0294047 | A1 | 11/2008 | Kodama et al. |
| 2008/0294209 | A1 | 11/2008 | Thompson et al. |
| 2009/0018425 | A1 | 1/2009 | Ouyang et al. |
| 2009/0024045 | A1 | 1/2009 | Prakash et al. |
| 2009/0076353 | A1 | 3/2009 | Carpenter et al. |
| 2009/0124875 | A1 | 5/2009 | Bentsen et al. |
| 2009/0156920 | A1 | 6/2009 | Kotzan et al. |
| 2009/0221885 | A1 | 9/2009 | Hall et al. |
| 2009/0259407 | A1 | 10/2009 | Gerlitz |
| 2009/0312973 | A1 | 12/2009 | Hatlestad et al. |
| 2010/0057057 | A1 | 3/2010 | Hayter et al. |
| 2010/0119760 | A1 | 5/2010 | Kirk et al. |
| 2010/0149544 | A1 | 6/2010 | Ghislain |
| 2010/0280578 | A1 | 11/2010 | Skelton et al. |
| 2010/0292634 | A1 | 11/2010 | Bilmes et al. |
| 2011/0024307 | A1 | 2/2011 | Simpson et al. |
| 2011/0098547 | A1 | 4/2011 | Zhu et al. |
| 2011/0130666 | A1 | 6/2011 | Dong et al. |
| 2012/0059232 | A1 | 3/2012 | Gross et al. |
| 2012/0116195 | A1 | 5/2012 | Chaum et al. |
| 2013/0060105 | A1 | 3/2013 | Shah et al. |
| 2013/0150689 | A1 | 6/2013 | Shaw-klein |
| 2013/0184599 | A1 | 7/2013 | Friedman et al. |
| 2013/0197332 | A1 | 8/2013 | Lucisano et al. |
| 2013/0338727 | A1 | 12/2013 | Mokelke et al. |
| 2014/0018644 | A1 | 1/2014 | Colvin et al. |
| 2014/0046152 | A1 | 2/2014 | Bechtel et al. |
| 2014/0091945 | A1 | 4/2014 | Rivas et al. |

(56) References Cited

U.S. PATENT DOCUMENTS

| | | | |
|---|---|---|---|
| 2014/0155710 | A1 | 6/2014 | Rowland et al. |
| 2014/0187878 | A1 | 7/2014 | Emken et al. |
| 2014/0276164 | A1 | 9/2014 | Thakur et al. |
| 2014/0286875 | A1 | 9/2014 | Gamsey et al. |
| 2014/0357964 | A1 | 12/2014 | Wisniewski et al. |
| 2014/0364758 | A1 | 12/2014 | Schindhelm et al. |
| 2015/0057509 | A1 | 2/2015 | Huffstetler et al. |
| 2015/0164383 | A1 | 6/2015 | Varsavsky et al. |
| 2015/0173655 | A1 | 6/2015 | Demmer et al. |
| 2015/0352229 | A1 | 12/2015 | Brill et al. |
| 2016/0256063 | A1 | 9/2016 | Friedman et al. |
| 2016/0363550 | A1 | 12/2016 | Koo et al. |
| 2016/0374597 | A1 | 12/2016 | Stahmann |
| 2017/0000359 | A1 | 1/2017 | Kohli et al. |
| 2017/0215732 | A1 | 8/2017 | Genier et al. |
| 2017/0245788 | A1 | 8/2017 | Heikenfeld |
| 2018/0055426 | A1 | 3/2018 | Kane et al. |
| 2018/0153451 | A1 | 6/2018 | Heikenfeld et al. |
| 2018/0263511 | A1 | 9/2018 | Burnes et al. |
| 2018/0344218 | A1 | 12/2018 | Li et al. |
| 2018/0350468 | A1 | 12/2018 | Friedman et al. |
| 2018/0364207 | A1 | 12/2018 | Roberts et al. |
| 2019/0029567 | A1 | 1/2019 | Stahmann et al. |
| 2019/0038190 | A1 | 2/2019 | Zhong et al. |
| 2019/0046032 | A1 | 2/2019 | Stahmann et al. |
| 2019/0059792 | A1 | 2/2019 | Kane et al. |
| 2019/0125228 | A1 | 5/2019 | Kane et al. |
| 2019/0167112 | A1 | 6/2019 | Kane et al. |
| 2019/0167162 | A1 | 6/2019 | Li et al. |
| 2019/0336050 | A1 | 11/2019 | Deck et al. |
| 2020/0029904 | A1 | 1/2020 | Kim |
| 2020/0061271 | A1 | 2/2020 | Potkay |
| 2020/0069949 | A1 | 3/2020 | Ghosh |
| 2021/0093235 | A1 | 4/2021 | DeSousa et al. |
| 2021/0401564 | A1 | 12/2021 | Neuenfeldt et al. |
| 2022/0133177 | A1 | 5/2022 | Li et al. |
| 2022/0133178 | A1 | 5/2022 | Li et al. |
| 2022/0133234 | A1 | 5/2022 | Li et al. |

FOREIGN PATENT DOCUMENTS

| | | |
|---|---|---|
| CN | 102333478 | 1/2012 |
| CN | 105530867 | 4/2016 |
| CN | 106028932 | 10/2016 |
| CN | 108968976 | 9/2022 |
| CN | 109381195 | 1/2023 |
| CN | 109419515 | 3/2023 |
| CN | 109864747 | 8/2023 |
| CN | 109864746 | 9/2023 |
| CN | 109717876 | 12/2023 |
| EP | 2967333 | 1/2016 |
| EP | 3409203 | 4/2021 |
| EP | 3495804 | 5/2022 |
| EP | 3492014 | 10/2022 |
| EP | 3440999 | 3/2023 |
| EP | 4236794 | 9/2023 |
| EP | 4236795 | 9/2023 |
| EP | 3672486 | 10/2023 |
| JP | 2005287762 | 10/2005 |
| JP | 2005315871 | 11/2005 |
| WO | 9625978 | 8/1996 |
| WO | 9719188 | 5/1997 |
| WO | 9801071 | 1/1998 |
| WO | 9902651 | 1/1999 |
| WO | 0025862 | 5/2000 |
| WO | 0025863 | 5/2000 |
| WO | 0180728 | 11/2001 |
| WO | 2004039265 | 5/2004 |
| WO | 2004071291 | 8/2004 |
| WO | 2004081522 | 9/2004 |
| WO | 2004091719 | 10/2004 |
| WO | 2004092713 | 10/2004 |
| WO | 2005074612 | 8/2005 |
| WO | 2006017169 | 2/2006 |
| WO | 2007110867 | 10/2007 |
| WO | 2007137037 | 11/2007 |
| WO | 2008076491 | 6/2008 |
| WO | 2009038996 | 3/2009 |
| WO | 2013016573 | 1/2013 |
| WO | 2015048514 | 4/2015 |

OTHER PUBLICATIONS

"Response to Non-Final Rejection," mailed on Apr. 29, 2025, for U.S. Appl. No. 17/510,802, submitted via Patent Center on Jul. 29, 2025, 11 pages.

"Communication Pursuant to Article 94(3) EPC," for European Patent Application No. 07762189.4 mailed Mar. 24, 2009 (3 pages).

"Communication pursuant to Article 94(3) EPC," for European Patent Application No. 07762189.4 mailed Mar. 16, 2010 (3 pages).

"Communication Pursuant to Article 94(3) EPC," for European Patent Application No. 18174561.3 mailed Jan. 27, 2020 (5 pages).

"Communication Pursuant to Article 94(3) EPC," for European Patent Application No. 18202201.2 mailed Nov. 9, 2022 (6 pages).

"Communication Pursuant to Article 94(3) EPC," for European Patent Application No. 18207668.7 mailed Aug. 4, 2020 (5 pages).

"Communication Pursuant to Article 94(3) EPC," for European Patent Application No. 18207668.7 mailed Jan. 13, 2021 (4 pages).

"Communication Pursuant to Article 94(3) EPC," for European Patent Application No. 18209525.7 mailed Dec. 8, 2020 (5 pages).

"Corrected Notice of Allowance," for U.S. Appl. No. 16/041,923 mailed Feb. 27, 2024 (5 pages).

"Extended European Search Report," for European Patent Application No. 18174561.3 mailed Aug. 28, 2018 (9 pages).

"Extended European Search Report," for European Patent Application No. 18188253.1 mailed Apr. 9, 2019 (10 pages).

"Extended European Search Report," for European Patent Application No. 18202201.2 mailed Jun. 28, 2019 (9 pages).

"Extended European Search Report," for European Patent Application No. 18207668.7 mailed Apr. 3, 2019 (7 pages).

"Extended European Search Report," for European Patent Application No. 18209525.7 mailed Feb. 27, 2019 (12 pages).

"Final Office Action," for U.S. Appl. No. 12/391,761 mailed Dec. 17, 2012 (15 pages).

"Final Office Action," for U.S. Appl. No. 15/992,823 mailed Aug. 13, 2020 (18 pages).

"Final Office Action," for U.S. Appl. No. 16/038,737 mailed Nov. 2, 2020 (15 pages).

"Final Office Action," for U.S. Appl. No. 16/038,737 mailed Sep. 7, 2021 (12 pages).

"Final Office Action," for U.S. Appl. No. 16/041,923 mailed Jul. 9, 2021 (29 pages).

"Final Office Action," for U.S. Appl. No. 16/041,923 mailed Oct. 16, 2023 (28 pages).

"Final Office Action," for U.S. Appl. No. 16/041,923 mailed Oct. 21, 2022 (31 pages).

"Final Office Action," for U.S. Appl. No. 16/106,623 mailed Dec. 2, 2021 (25 pages).

"Final Office Action," for U.S. Appl. No. 16/130,638 mailed Jan. 26, 2022 (16 pages).

"Final Office Action," for U.S. Appl. No. 16/130,638 mailed Nov. 2, 2022 (12 pages).

"Final Office Action," for U.S. Appl. No. 16/130,638 mailed Oct. 31, 2023 (18 pages).

"Final Office Action," for U.S. Appl. No. 16/136,875 mailed Aug. 21, 2020 (10 pages).

"Final Office Action," for U.S. Appl. No. 17/510,802 mailed Oct. 5, 2023 (13 pages).

"First Examination Report," for Australian Patent Application No. 2008302499 mailed Feb. 8, 2011 (1 page).

"First Office Action," for Chinese Patent Application No. 201710400287.0 mailed Dec. 23, 2021 (37 pages) with English Translation.

"First Office Action," for Chinese Patent Application No. 201710681567.3 mailed Mar. 18, 2022 (16 pages) with English Translation.

(56) References Cited

OTHER PUBLICATIONS

"First Office Action," for Chinese Patent Application No. 201710730979.1 mailed Apr. 11, 2022 (23 pages) with English Translation.
"First Office Action," for Chinese Patent Application No. 201711052948.1 mailed Oct. 28, 2022 (21 pages) with English Translation.
"First Office Action," for Chinese Patent Application No. 201711249985.1 mailed Feb. 27, 2023 (11 pages), with English translation.
"First Office Action," for Chinese Patent Application No. 201711266579.6 mailed Jan. 5, 2023 (10 pages) No English Translation.
"International Preliminary Report on Patentability," for PCT Application No. PCT/US2008/075673 mailed Mar. 24, 2010 (6 pages).
"International Preliminary Report on Patentability," for PCT Application No. PCT/US2018/043225 mailed Feb. 6, 2020 (7 pages).
"International Preliminary Report on Patentability," for PCT Application No. PCT/US2018/047549 mailed Mar. 5, 2020 (11 pages).
"International Preliminary Report on Patentability," for PCT Application No. PCT/US2021/056590 mailed May 11, 2023 (9 pages).
"International Preliminary Report on Patentability," for PCT Application No. PCT/US2021/056602 mailed May 11, 2023 (8 pages).
"International Search Report and Written Opinion," for PCT Application No. PCT/US2008/075673 mailed Nov. 28, 2008 (13 pages).
"International Search Report and Written Opinion," for PCT Application No. PCT/US2018/043225 mailed Nov. 16, 2018 (11 pages).
"International Search Report and Written Opinion," for PCT Application No. PCT/US2018/047549 mailed Oct. 26, 2018 (15 pages).
"International Search Report and Written Opinion," for PCT Application No. PCT/US2021/056590 mailed May 3, 2022 (14 pages).
"International Search Report and Written Opinion," for PCT Application No. PCT/US2021/056602 mailed Feb. 9, 2022 (12 pages).
"Invitation to Pay Additional Fees," for PCT Application No. PCT/US2021/056590 mailed Mar. 9, 2022 (9 pages).
"Microminiature Device Monitors Vital Electrolytes and Metabolites," John Glenn Biomedical Engineering Consortium, May 2002 (2 pages).
"Microminiature Monitor for Vital Electrolyte and Metabolite Levels of Astronauts—Status Report," John Glenn Biomedical Engineering Consortium NASA Glenn Research Center at Lewis Field, Apr. 2003 (5 pages).
"Non-Final Office Action," for U.S. Appl. No. 12/391,761, mailed May 22, 2014 (16 pages).
"Non-Final Office Action," for U.S. Appl. No. 12/391,761 mailed Jul. 9, 2012 (15 pages).
"Non-Final Office Action," for U.S. Appl. No. 15/992,823 mailed Dec. 23, 2020 (18 pages).
"Non-Final Office Action," for U.S. Appl. No. 15/992,823 mailed May 5, 2020 (51 pages).
"Non-Final Office Action," for U.S. Appl. No. 16/038,737 mailed Jun. 22, 2020 (46 pages).
"Non-Final Office Action," for U.S. Appl. No. 16/038,737 mailed Mar. 3, 2022 (17 pages).
"Non-Final Office Action," for U.S. Appl. No. 16/038,737 mailed Mar. 24, 2021 (14 pages).
"Non-Final Office Action," for U.S. Appl. No. 16/041,923 mailed Feb. 2, 2021 (39 pages).
"Non-Final Office Action," for U.S. Appl. No. 16/041,923 mailed Jul. 23, 2020 (61 pages).
"Non-Final Office Action," for U.S. Appl. No. 16/041,923 mailed Mar. 29, 2023 (25 pages).
"Non-Final Office Action," for U.S. Appl. No. 16/041,923 mailed May 23, 2022 (22 pages).
"Non-Final Office Action," for U.S. Appl. No. 16/041,923 mailed Nov. 15, 2021 (21 pages).
"Non-Final Office Action," for U.S. Appl. No. 16/106,623 mailed Aug. 25, 2021 (31 pages).
"Non-Final Office Action," for U.S. Appl. No. 16/106,623 mailed Jun. 24, 2022 (19 pages).
"Non-Final Office Action," for U.S. Appl. No. 16/106,623 mailed Oct. 9, 2020 (60 pages).
"Non-Final Office Action," for U.S. Appl. No. 16/130,638 mailed Aug. 23, 2021 (67 pages).
"Non-Final Office Action," for U.S. Appl. No. 16/130,638 mailed May 6, 2022 (13 pages).
"Non-Final Office Action," for U.S. Appl. No. 16/130,638 mailed May 18, 2023 (13 pages).
"Non-Final Office Action," for U.S. Appl. No. 16/136,773 mailed Jun. 1, 2020 (43 pages).
"Non-Final Office Action," for U.S. Appl. No. 16/136,875 mailed Jan. 25, 2021 (12 pages).
"Non-Final Office Action," for U.S. Appl. No. 16/136,875 mailed May 27, 2020 (43 pages).
"Non-Final Office Action," for U.S. Appl. No. 17/510,802 mailed Apr. 24, 2024 (26 pages).
"Non-Final Office Action," for U.S. Appl. No. 17/510,802 mailed Jun. 1, 2023 (52 pages).
"Non-Final Office Action," for U.S. Appl. No. 17/510,903 mailed Aug. 16, 2023 (55 pages).
"Non-Final Office Action," for U.S. Appl. No. 17/510,903 mailed Dec. 12, 2023 (17 pages).
"Non-Final Office Action," for U.S. Appl. No. 17/510,903 mailed May 22, 2024 (17 pages).
"Non-Final Office Action," mailed on May 27, 2020 for U.S. Appl. No. 16/136,875, 43 pages.
"Notice of Allowance," for U.S. Appl. No. 15/992,823 mailed Jun. 10, 2021 (16 pages).
"Notice of Allowance," for U.S. Appl. No. 16/038,737 mailed May 18, 2022 (13 pages).
"Notice of Allowance," for U.S. Appl. No. 16/041,923 mailed Feb. 14, 2024 (13 pages).
"Notice of Allowance," for U.S. Appl. No. 16/106,623 mailed Oct. 13, 2022 (11 pages).
"Notice of Allowance," for U.S. Appl. No. 16/136,773 mailed Nov. 18, 2020 (17 pages).
"Notice of Allowance," for U.S. Appl. No. 16/136,875 mailed Apr. 15, 2021 (13 pages).
"Office Action," for Japanese Patent Application No. 2010-524940 mailed Nov. 22, 2011 (8 pages) with English translation.
"Partial European Search Report," for European Patent Application No. 18188253.1 mailed Jan. 7, 2019 (11 pages).
"PCT International Search Report and Written Opinion," for International Application No. PCT/US2007/068954, mailed Nov. 17, 2008 (12 pages).
"Response to Communication Pursuant to Article 94(3) EPC," for European Patent Application No. 07762189.4 filed with the EPO Jul. 27, 2009 (8 pages).
"Response to Communication Pursuant to Article 94(3) EPC," for European Patent Application No. 18174561.3 filed Jul. 27, 2020 (11 pages).
"Response to Communication Pursuant to Article 94(3) EPC," for European Patent Application No. 18202201.2 filed Mar. 17, 2023 (33 pages).
"Response to Communication Pursuant to Article 94(3) EPC," for European Patent Application No. 18207668.7 filed Dec. 11, 2020 (65 pages).
"Response to Communication Pursuant to Article 94(3) EPC," for European Patent Application No. 18207668.7 filed May 21, 2021 (32 pages).
"Response to Communication Pursuant to Article 94(3) EPC," for European Patent Application No. 18209525.7 filed Apr. 15, 2021 (10 pages).
"Response to Communication Pursuant to Rule 69 EPC," for European Patent Application No. 18174561.3 filed Jun. 3, 2019 (21 pages).
"Response to Communication Pursuant to Rule 69 EPC," for European Patent Application No. 18202201.2 filed Jan. 31, 2020 (22 pages).
"Response to Communication Pursuant to Rule 69 EPC," for European Patent Application No. 18209525.7 filed with the EPO Dec. 12, 2019 (33 pages).

(56) References Cited

OTHER PUBLICATIONS

"Response to Communication Pursuant to Rules 161(1) and 162 EPC," for EP Patent Application No. 21823395.5 mailed Dec. 4, 2023 (13 pages).
"Response to Communication Pursuant to Rules 161(1) and 162 EPC," for European Patent Application No. 18773017.1 filed Sep. 30, 2020 (13 pages).
"Response to Communication Pursuant to Rules 161(1) and 162 EPC," for European Patent Application No. 21823397.1 filed Dec. 6, 2023 (12 pages).
"Response to European Search Report," for European Patent Application No. 18188253.1 filed Nov. 7, 2019 (14 pages).
"Response to Extended European Search Report," for European Patent Application No. 18207668.7 filed Nov. 29, 2019 (14 pages).
"Response to Final Office Action," mailed on Oct. 21, 2022 for U.S. Appl. No. 16/041,923, submitted via EFS-Web on Jan. 20, 2023 (9 pages).
"Response to Final Rejection," mailed Jan. 26, 2022 and the Advisory Action mailed on Apr. 18, 2022 for U.S. Appl. No. 16/130,638, submitted via EFS-Web on Apr. 26, 2022, 7 pages.
"Response to Final Rejection," mailed Jan. 26, 2022 for U.S. Appl. No. 16/130,638, submitted via EFS-Web on Mar. 24, 2022, 8 pages.
"Response to Final Rejection," mailed on Aug. 13, 2020 for U.S. Appl. No. 15/992,823, submitted via EFS-Web on Oct. 13, 2020, 9 pages.
"Response to Final Rejection," mailed on Aug. 21, 2020 and Advisory Action received on Oct. 19, 2020 for U.S. Appl. No. 16/136,875, submitted via EFS-Web on Nov. 20, 2020, 14 pages.
"Response to Final Rejection," mailed on Aug. 21, 2020 for U.S. Appl. No. 16/136,875, submitted via EFS-Web on Oct. 13, 2020, 12 pages.
"Response to Final Rejection," mailed on Dec. 2, 2021 and the Advisory Action mailed on Apr. 5, 2022 for U.S. Appl. No. 16/106,623, submitted via EFS-Web on May 2, 2022, 14 pages.
"Response to Final Rejection," mailed on Dec. 2, 2021 for U.S. Appl. No. 16/106,623, submitted via EFS-Web on Feb. 24, 2022, 14 pages.
"Response to Final Rejection," mailed on Jul. 9, 2021 and Advisory Action mailed on Sep. 20, 2021 for U.S. Appl. No. 16/041,923, submitted via EFS-Web on Sep. 27, 2021, 12 pages.
"Response to Final Rejection," mailed on Jul. 9, 2021 for U.S. Appl. No. 16/041,923, submitted via EFS-Web on Sep. 9, 2021, 12 pages.
"Response to Final Rejection," mailed on Nov. 2, 2020 for U.S. Appl. No. 16/038,737, submitted via EFS-Web on Feb. 2, 2021, 9 pages.
"Response to Final Rejection," mailed on Nov. 2, 2022 and the Advisory Action mailed on Mar. 17, 2023 for U.S. Appl. No. 16/130,638, submitted via EFS-Web on Apr. 3, 2023, 9 pages.
"Response to Final Rejection," mailed on Nov. 2, 2022 for U.S. Appl. No. 16/130,638, submitted via EFS-Web on Feb. 1, 2023, 8 pages.
"Response to Final Rejection," mailed on Oct. 16, 2023, for U.S. Appl. No. 16/041,923, submitted via EFS-Web on Jan. 16, 2024, 5 pages.
"Response to Final Rejection," mailed on Oct. 5, 2023, and the Advisory Action mailed on Jan. 17, 2024, in U.S. Appl. No. 17/510,802, submitted via EFS-Web on Jan. 29, 2024, 10 pages.
"Response to Final Rejection," mailed on Oct. 5, 2023, for U.S. Appl. No. 17/510,802, submitted via EFS-Web on Jan. 4, 2024, 10 pages.
"Response to Final Rejection," mailed on Sep. 7, 2021 for U.S. Appl. No. 16/038,737, submitted via EFS-Web on Nov. 30, 2021, 10 pages.
"Response to Non-Final Rejection," mailed on Aug. 16, 2023, for U.S. Appl. No. 17/510,903, submitted via EFS-Web on Nov. 16, 2023, 14 pages.
"Response to Non-Final Rejection," mailed on Aug. 23, 2021 for U.S. Appl. No. 16/130,638, submitted via EFS-Web on Nov. 1, 2021, 9 pages.
"Response to Non-Final Rejection," mailed on Aug. 25, 2021 for U.S. Appl. No. 16/106,623, submitted via EFS-Web on Oct. 27, 2021, 14 pages.
"Response to Non-Final Rejection," mailed on Dec. 12, 2023, for U.S. Appl. No. 17/510,903, submitted via EFS-Web on Mar. 12, 2024, 11 pages.
"Response to Non-Final Rejection," mailed on Dec. 23, 2020 for U.S. Appl. No. 15/992,823, submitted via EFS-Web on Mar. 23, 2021, 9 pages.
"Response to Non-Final Rejection," mailed on Feb. 2, 2021 for U.S. Appl. No. 16/041,923, submitted via EFS-Web on Mar. 17, 2021, 12 pages.
"Response to Non-Final Rejection," mailed on Jan. 25, 2021 for U.S. Appl. No. 16/136,875, submitted via EFS-Web on Mar. 17, 2021, 12 pages.
"Response to Non-Final Rejection," mailed on Jul. 23, 2020 for U.S. Appl. No. 16/041,923, submitted via EFS-Web on Oct. 13, 2020, 12 pages.
"Response to Non-Final Rejection," mailed on Jun. 1, 2020 for U.S. Appl. No. 16/136,773, submitted via EFS-Web on Aug. 20, 2020, 10 pages.
"Response to Non-Final Rejection," mailed on Jun. 1, 2023, for U.S. Appl. No. 17/510,802, submitted via EFS-Web on Aug. 31, 2023, 9 pages.
"Response to Non-Final Rejection," mailed on Jun. 22, 2020 for U.S. Appl. No. 16/038,737, submitted via EFS-Web on Aug. 4, 2020, 10 pages.
"Response to Non-Final Rejection," mailed on Jun. 24, 2022 for U.S. Appl. No. 16/106,623, submitted via EFS-Web on Sep. 22, 2022, 7 pages.
"Response to Non-Final Rejection," mailed on Mar. 24, 2021 for U.S. Appl. No. 16/038,737, submitted via EFS-Web on Jun. 18, 2021, 11 pages.
"Response to Non-Final Rejection," mailed on Mar. 29, 2023, for U.S. Appl. No. 16/041,923, submitted via EFS-Web on Jun. 29, 2023, 14 pages.
"Response to Non-Final Rejection," mailed on Mar. 3, 2022 for U.S. Appl. No. 16/038,737, submitted via EFS-Web on May 4, 2022, 10 pages.
"Response to Non-Final Rejection," mailed on May 18, 2023, for U.S. Appl. No. 16/130,638, submitted via EFS-Web on Aug. 17, 2023, 12 pages.
"Response to Non-Final Rejection," mailed on May 23, 2022 for U.S. Appl. No. 16/041,923, submitted via EFS-Web on Aug. 23, 2022, 11 pages.
"Response to Non-Final Rejection," mailed on May 27, 2020 for U.S. Appl. No. 16/136,875, submitted via EFS-Web on Jul. 22, 2020, 11 pages.
"Response to Non-Final Rejection," mailed on May 5, 2020 for U.S. Appl. No. 15/992,823, submitted via EFS-Web on Jul. 7, 2020, 10 pages.
"Response to Non-Final Rejection," mailed on May 6, 2022 for U.S. Appl. No. 16/130,638, submitted via EFS-Web on Aug. 5, 2022, 7 pages.
"Response to Non-Final Rejection," mailed on Nov. 15, 2021 for U.S. Appl. No. 16/041,923, submitted via EFS-Web on Feb. 9, 2022, 7 pages.
"Response to Non-Final Rejection," mailed on Oct. 9, 2020 for U.S. Appl. No. 16/106,623, submitted via EFS-Web on Jan. 8, 2021, 21 pages.
"Restriction Requirement mailed," Feb. 17, 2012 in co-pending U.S. Appl. No. 12/391,761, "Optical Window Assembly for Implantable Medical Device," (5 pages)., 5.
"Second Office Action," for Chinese Patent Application No. 201710730979.1 mailed Oct. 21, 2022 (3 pages) no English Translation.
"Second Office Action," for Chinese Patent Application No. 201711052948.1 mailed May 17, 2023 (11 pages) with English translation.
"Upconverting nanoparticles," Wikipeda.com accessed Jun. 12, 2017 (13 pages).

(56) References Cited

OTHER PUBLICATIONS

Anderson, J. M., et al."Monocyte, Macrophage and foreign body giant cell interactions with molecularly engineered surfaces," Journal of Materials Science: Materials in Medicine 10 (1999) 579-588 (10 pages).
Anderson, James M."Biological Responses to Materials," Annu. Rev. Mater. Res. 2001. 31:81-110 (30 pages).
Anderson, James M., et al."Foreign Body Reaction to Biomaterials," Semin. Immunol. Apr. 2008; 20(2): 86-100 (27 pages).
Bakker, Eric, et al."Carrier-Based Ion-Selective Electrodes and Bulk Optodes. 1. General Characteristics," Chem. Rev. 1997, 97, 3083-3132 (50 pages).
Bansal, Vinod K."Serum Inorganic Phosphorus," In: Walker HK, Hall WD, Hurst JW, editors. Clinical Methods: The History, Physical, and Laboratory Examinations. 3rd ed. (1990) Boston: Butterworths; 1990. Chapter 198. PMID 21250152 (6 pages).
Benco, John S., et al."Optical Sensors for Blood Analytes," The Spectrum, vol. 14, Issue 4, pp. 4-11, Winter 2001 (8 pages).
Bender, J. W., et al."The Use of Biomedical Sensors to Monitor Capsule Formation Around Soft Tissue Implants," Annals of Plastic Surgery, vol. 56, No. 1, Jan. 2006, pp. 72-77 (6 pages).
Bridges, Amanda W., et al."Anti-Inflammatory Polymeric Coatings for Implantable Biomaterials and Devices," Journal of Diabetes Science and Technology 2008;2(6):984-994 (11 pages).
Buhlmann, Philippe, et al."Carrier-Based Ion-Selective Electrodes and Bulk Optodes. 2. Ionophores for Potentiometric and Optical Sensors," Chem. Rev. 1998, 98, 1593-1687 (95 pages).
Han, In Suk, et al."Constant-Volume Hydrogel Osmometer: A New Device Concept for Miniature Biosensors," Biomacromolecules, Mar. 2002, pp. 1271-1275 (5 pages).
He, Huarui, et al."Enantioselective Optodes," Analytica Chimica Acta, 246, pp. 251-257, 1991 (7 pages).
He, Wei, et al."A Novel Anti-inflammatory Surface for Neural Electrodes," Adv. Mater. 2007, 19, 3529-3533 (5 pages).
Helton, Kristen L., et al. "Biomechanics of the Sensor-Tissue Interface-Effects of Motion, Pressure, and Design on Sensor Performance and the Foreign Body Response—Part I: Theoretical Framework," Journal of Diabetes Science and Technology 2011;5(3):632-646 (15 pages).
Kane, Michael J., et al. "Implantable Medical Device Header with Optical Interface," U.S. Appl. No. 11/533,948.
Kane, Michael J., et al."Implantable Medical Device with Chemical Sensor and Related Methods," U.S. Appl. No. 11/383,926.
Kane, Michael J., et al."Implantable Medical Device with Chemical Sensor and Related Methods," U.S. Appl. No. 11/383,933.
Kane, Michael John, et al."Implantable Medical Device Header with Optical Interface," U.S. Appl. No. 11/533,948.
Kane, Michael John, et al."Implantable Medical Device with Chemical Sensor and Related Methods," U.S. Appl. No. 11/383,926.
Kane, Michael John, et al."Implantable Medical Device with Chemical Sensor and Related Methods," U.S. Appl. No. 11/383,933.
Koh, Ahyeon, et al."Glucose Sensor Membranes for Mitigating the Foreign Body Response," Journal of Diabetes Science and Technology 2011;5(5):1052-1059 (8 pages).
Koronczi, et al."Development of a submicron optochemical potassium sensor with enhanced stability due to internal reference," Sensors and Actuators B, 51:188-195 (1998).
Kuwana, Eddy, et al."Sensing of pH in Multiply Scattering Media with Fluorescence Lifetime," Advanced Biomedical and Clinical Diagnostic Systems, Proceedings of SPIE, vol. 4958, pp. 32-42, 2003 (11 pages).
Lehn, J. M., et al."[2]-Cryptates: Stability and Selectivity of Alkali and Akaline-Earth Macrobicycle Complexes," Journal of the American Chemical Society, Nov. 12, 1975 pp. 6700-6707 (8 pages).
Lima-Oliveira, Gabriel, et al."Patient Posture for Blood Collection by Venipuncture: Recall for Standardization After 28 Years," Brazilian Journal of Hematology and Hemotherapy 2017 <http://dx.doi.org/10.1016/j.bjhh.2017.01.004> (6 pages).
Messler "The Joining of Materials," Nov. 2004 (58 pages).
Novak, Matthew T., et al. "Modeling the relative impact of capsular tissue effects on implanted glucose sensor time lag and signal attenuation," Anal. Bioanal. Chem. Oct. 2010; 398(4):1695-1705 (22 pages).
Padmanabhan, Jagnnath, et al."Nanomaterials, Inflammation and Tissue Engineering," Wiley Interdiscip Rev Nanomed Nanobiotechnol. May 2015; 7(3):355-370 (23 pages).
Renoe, Brian W., et al."Influence of Posture on Free Calcium and Related Variables," Clinical Chemistry, vol. 25, Issue 10, Oct. 1, 1979, 1766-1769 (5 pages).
Roger, Yvonne, et al."Grid-like surface structures in thermoplastic polyurethane induce anti-inflammatory and anti-fibrotic processes in bone marrow-derived mesenchymal stem cells," Abstract Only Colloids and Surfaces B: Biointerfaces vol. 148, Dec. 2016, pp. 104-115 (4 pages).
Seelig, Mildred S."Electrographic Patterns of Magnesium Depletion Appearing in Alcoholic Heart Disease," Annals of the New York Academy of Sciences, vol. 162, Article 2, 1969, pp. 906-917 (13 pages).
Sharkawy, A. Adam, et al."Engineering the tissue which encapsulates subcutaneous implants. I. Diffusion properties," Department of Biomedical Engineering, NSF Center for Emerging Cardiovascular Technology, Duke University, Durham, North Carolina 1996 (12 pages).
Shirreffs, S. M."The Effect of Posture Change on Blood Volume, Serum Potassium, and Whole Body Electrical Impedance," Eur. J. Appl. Physiol. (1994)69:461-463 (3 pages).
Statland, Bernard E., et al."Factors Contributing to Intra-Individual Variation of Serum Constituents: 4. Effects of Posture and Tourniquet Application on Variation of Serum Constituents in Healthy Subjects," Clinical Chemistry, 20(12), 1513-1519 (1974), doi.org/10/1093/clinchem/20.12.1513 (7 pages).
Tohda, Koji, et al."A Microscopic, Continuous, Optical Monitor for Interstitial Electrolytes and Glucose," Chemphyschem 2003, pp. 155-160 (6 pages).
Tohda, Koji, et al."Micro-miniature Autonomous Optical Sensor Array for Monitoring Ions and Metabolites 1: Design, Fabrication, and Data Analysis," Analytical Sciences, Mar. 2006, vol. 22 pp. 383-388 (6 pages).
Tsai, Hc, et al."Simultaneous Determination of Renal Clinical Analytes in Serum using Hydrolase- and Oxidase-Encapsulated Optical Array Biosensors," Analytical Biochemistry 334 (2004) 183-192 (10 pages).
Voskerician, Gabriela, et al."Biocompatibility and Biofouling of MEMs Drug Delivery Devices," Biomaterials 24 (2003) 1959-1967 (9 pages).
Weisberg, Lawrence S."Management of Severe Hyperkalemia," Crit Care Med 2008 vol. 36, No. 12 (6 pages).
Yu, J.H., et al."In-situ analysis of thermal properties of polymer composites by embedded LED temperature sensor," Microelectronics Journal, vol. 44, Issue 11 [online]. Nov. 2013 [retrieved on May 15, 2024] Retrieved from the Internet <URL: https//www.sciencedirect.com/science/article/pii/S0026269213000232> (Year: 2013) <DOI: https://doi.org/10.1016/j.mejo.2013.01.010>, pp. 1025-1028.
"Final Office Action," for U.S. Appl. No. 17/510,806 mailed Aug. 28, 2025 (18 pages).
"Response to Non-Final Rejection," mailed on May 19, 2025, for U.S. Appl. No. 17/510,903, submitted via Patent Center on Aug. 19, 2025, 11 pages.
"Corrected Notice of Allowability," for U.S. Appl. No. 17/510,903 mailed Jan. 13, 2026 (5 pages).
"Final Office Action," for U.S. Appl. No. 17/510,802 mailed Nov. 6, 2025 (22 pages).
"Non-Final Office Action," for U.S. Appl. No. 17/510,806 mailed Dec. 23, 2025 (26 pages).
"Notice of Allowance," for U.S. Appl. No. 17/510,903 mailed Nov. 4, 2025 (16 pages).
"Response to Final Rejection," mailed on Aug. 28, 2025, for U.S. Appl. No. 17/510,806, submitted via Patent Center on Nov. 21, 2025, 10 pages.

(56) References Cited

OTHER PUBLICATIONS

"Final Office Action," for U.S. Appl. No. 17/510,903 mailed Nov. 15, 2024 (26 pages).
"Response to Final Rejection," mailed on Sep. 12, 2024, for U.S. Appl. No. 17/510,802, submitted via EFS-Web on Dec. 11, 2024, 12 pages.
"Response to Non Final Office Action," for U.S. Appl. No. 17/510,903, filed Aug. 22, 2024 (11 pages).
"Response to Non-Final Rejection," mailed on Apr. 24, 2024, for U.S. Appl. No. 17/510,802, submitted via EFS-Web on Jul. 24, 2024, 11 pages.
"Non-Final Office Action," for U.S. Appl. No. 17/510,802 mailed Apr. 29, 2025 (21 pages).
"Non-Final Office Action," for U.S. Appl. No. 17/510,806 mailed Feb. 11, 2025 (64 pages).
"Response to Final Rejection," mailed on Nov. 15, 2024, for U.S. Appl. No. 17/10,903, submitted via EFS-Web on Feb. 12, 2025, 11 pages.
Nacht, Barbara, et al. "Integrated catheter system for continuous glucose measurement and simultaneous insulin infusion," Biosensors and Bioelectronics, 64 (2015): 102-110.
Susanto, Heru, et al. "Photografted Thin Polymer Hydrogel Layers on PES Ultrafiltration Membranes: Characterization, Stability, and Influence on Separation Performance.," Langmuir, 2007, 23 (14): 7818-7830.
"Response to Non-Final Rejection," mailed on Feb. 11, 2025, for U.S. Appl. No. 17/510,806, submitted via Patent Center on May 9, 2025, 12 pages.
"Final Office Action," for U.S. Appl. No. 17/510,806 mailed Apr. 27, 2026 (26 pages).
"Response to Non-Final Rejection," mailed on Dec. 23, 2025, for U.S. Appl. No. 17/510,806, submitted via Patent Center on Mar. 23, 2026, 12 pages.
"Non-Final Office Action," for U.S. Appl. No. 17/510,802 mailed Mar. 11, 2026 (22 pages).
"Response to Final Office Action," mailed on Nov. 6, 2025, for U.S. Appl. No. 17/510,802, submitted via Patent Center on Feb. 6, 2026, 12 pages.

STRUCTURAL DIFFUSION MEMBRANES FOR CHEMICAL SENSORS

This application is a continuation application of U.S. application Ser. No. 16/130,638, filed Sep. 13, 2018, which claims the benefit of China Patent Application No. 201711052948.1, filed Oct. 31, 2017, the contents of which are herein incorporated by reference in their entirety.

FIELD

Embodiments herein relate to implantable chemical sensors for detecting a physiological analyte and medical devices including the same.

BACKGROUND

Medical professionals frequently need to evaluate chemical analyte concentrations of a patient when assessing the patient's condition and/or diagnosing a problem. However, measuring physiological concentrations of analytes, such as potassium amongst others, generally requires drawing blood from the patient. Blood draws are commonly done at a medical clinic or hospital and therefore generally require the patient to physically visit a medical facility. As a result, despite their significance, physiological analyte concentrations are frequently measured only sporadically.

Implanted chemical sensors offer the promise of being able to gather data on analyte concentrations in real time even while a patient is away from a medical treatment facility. For example, implanted chemical sensors can measure analyte concentrations from the interstitial fluid as the analyte passes through a soft hydrophilic diffusion membrane and into a chemical sensor. The measurements can occur continuously or semi-continuously providing a far richer data set for a medical professional to evaluate.

SUMMARY

Embodiments herein relate to implantable chemical sensors for detecting a physiological analyte and medical devices including the same. In a first aspect, in addition to one or more of the preceding or following aspects, or in the alternative to some aspects, an implantable medical device is included. The implantable medical device can include a chemical sensor configured to detect an ion concentration in a bodily fluid. The chemical sensor can include a sensing element. The sensing element can include an outer barrier layer forming a top, a bottom, and opposed sides of the sensing element and a structural reinforcing element contacting the outer barrier layer. The top of the outer barrier layer of the sensing element can include a polymeric matrix permeable to analytes.

In a second aspect, in addition to one or more of the preceding or following aspects, or in the alternative to some aspects, a structural reinforcing element can be disposed beneath, within, or on top of the top of the outer barrier layer.

In a third aspect, in addition to one or more of the preceding or following aspects, or in the alternative to some aspects, a structural reinforcing element can be formed of polyester, polyurethane, polyethylene, polypropylene, nylon, sintered titanium, deep reactive-ion etched silicon, sintered stainless steel, sintered silica, liquid crystal, glass, borosilicate glass, or mixtures or derivatives thereof.

In a fourth aspect, in addition to one or more of the preceding or following aspects, or in the alternative to some aspects, a structural reinforcing element can be formed of a woven material.

In a fifth aspect, in addition to one or more of the preceding or following aspects, or in the alternative to some aspects, a structural reinforcing element can include one or more intramural struts spanning a distance between the top and the bottom of the outer barrier layer.

In a sixth aspect, in addition to one or more of the preceding or following aspects, or in the alternative to some aspects, the one or more intramural struts can be formed of polyester, polyurethane, polyethylene, polypropylene, nylon, sintered titanium, deep reactive-ion etched silicon, sintered stainless steel, sintered silica, liquid crystal, glass, borosilicate glass, or mixtures or derivatives thereof.

In a seventh aspect, in addition to one or more of the preceding or following aspects, or in the alternative to some aspects, an outer barrier layer can be formed of polyHEMA, agarose, alginates, polyvinyl alcohol, polyacrylate, collagen, PEG, gelatin, glass, borosilicate glass, or mixtures or derivatives thereof.

In an eighth aspect, in addition to one or more of the preceding or following aspects, or in the alternative to some aspects, the implantable medical device can include an optical excitation assembly configured to illuminate the sensing element; and an optical detection assembly configured to receive light from the sensing element.

In a ninth aspect, in addition to one or more of the preceding or following aspects, or in the alternative to some aspects, a chemical sensor can have a diameter that is greater than 1.0 mm.

In a tenth aspect, in addition to one or more of the preceding or following aspects, or in the alternative to some aspects, a chemical sensor can be configured to detect an ion selected from the group consisting of potassium, sodium, chloride, calcium, magnesium, lithium, or hydronium.

In an eleventh aspect, in addition to one or more of the preceding or following aspects, or in the alternative to some aspects, an implantable medical device is included. The implantable medical device can include a chemical sensor configured to detect an ion concentration in a bodily fluid. The chemical sensor can include a sensing element. The sensing element can include an outer barrier layer forming a top, a bottom, and opposed sides of the sensing element, where the outer barrier layer defines an interior volume. The sensing element can also include a structural reinforcing element disposed within the interior volume, where the structural reinforcing element is porous.

In a twelfth aspect, in addition to one or more of the preceding or following aspects, or in the alternative to some aspects, a structural reinforcing element can fill at least between 10% to 25% of the interior volume.

In a thirteenth aspect, in addition to one or more of the preceding or following aspects, or in the alternative to some aspects, a structural reinforcing element can be formed of a polyester, polyurethane, polyethylene, polypropylene, nylon, sintered titanium, deep reactive-ion etched silicon, sintered stainless steel, sintered silica, liquid crystal, glass, borosilicate glass, or mixtures or derivatives thereof.

In a fourteenth aspect, in addition to one or more of the preceding or following aspects, or in the alternative to some aspects, a structural reinforcing element can be formed of a borosilicate glass.

In a fifteenth aspect, in addition to one or more of the preceding or following aspects, or in the alternative to some aspects, an outer barrier layer can be formed of polyHEMA, agarose, alginates, polyvinyl alcohol, polyacrylate, collagen, PEG, gelatin, glass, borosilicate glass, or mixtures or derivatives thereof.

In a sixteenth aspect, in addition to one or more of the preceding or following aspects, or in the alternative to some aspects, an outer barrier layer can be formed of a glass.

In a seventeenth aspect, in addition to one or more of the preceding or following aspects, or in the alternative to some aspects, an outer barrier layer can be formed of a borosilicate glass.

In an eighteenth aspect, in addition to one or more of the preceding or following aspects, or in the alternative to some aspects, the bottom of an outer barrier layer can include a glass interface plate for coupling the sensing element to an optical excitation assembly and an optical detection assembly.

In a nineteenth aspect, in addition to one or more of the preceding or following aspects, or in the alternative to some aspects, the top of the outer barrier layer can be formed of polyHEMA.

In a twentieth aspect, in addition to one or more of the preceding or following aspects, or in the alternative to some aspects, a structural reinforcing element can be infused with one or more ion selective sensors.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

Implanted chemical sensors offer the promise of being able to gather data on analyte concentrations in real time even while a patient is away from a medical treatment facility.

Highly-porous soft hydrophilic polymers are ideal materials for use with implanted chemical sensors because of their ability to permit the rapid transport of large amounts of analytes across sensor walls and thus contribute to rapid response times for sensors built using the same. However, many such materials lack desirable levels of structural integrity. Such materials are generally soft and flexible which can lead to challenges when designing sensor elements, especially as the sensors get larger. In particular, the use of such materials in a chemical sensor can resulting in undesirable deformation and/or structural failure and interference at the optical interface of the chemical sensor, which can lead to diminished response and/or loss of function of the chemical sensor.

Embodiments herein, however, can include structural reinforcing elements that can provide structural integrity to soft hydrophilic diffusion membranes of chemical sensors. Thus, by including structural reinforcing elements, chemical sensors made using soft hydrophilic materials can maintain their structural integrity over the lifetime of the sensor.

Figure 1:
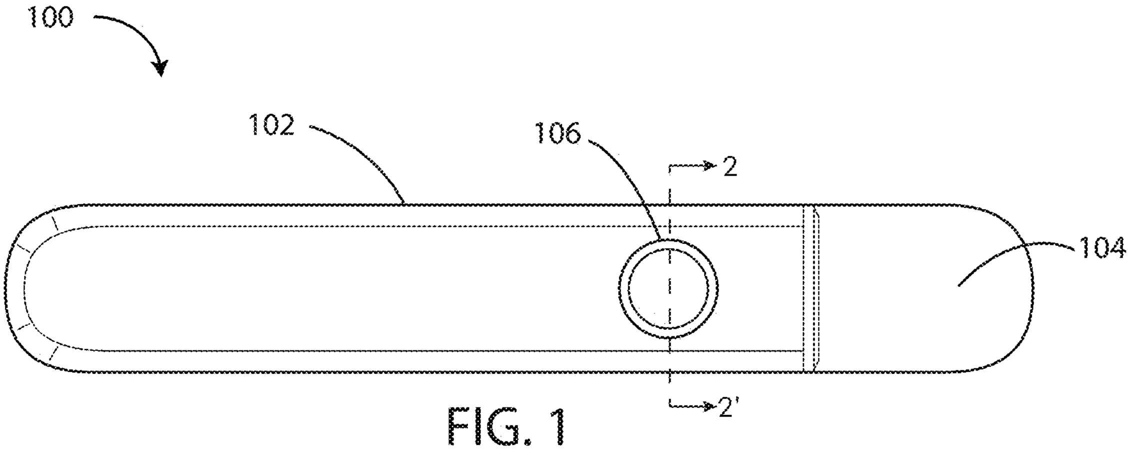
FIG. 1 is a schematic top view of an implantable medical device in accordance with the embodiments herein.

Referring now to FIG. 1, an implantable medical device (IMD) 100 is shown in accordance with the embodiments herein. The IMD 100 can include an implantable housing 102 and a header 104 coupled to the implantable housing 102. Various materials can be used. However, in some embodiments, the housing 102 can be formed of a material such as a metal, ceramic, a polymer, or a composite. The header 104 can be formed of various materials, but in some embodiments the header 104 can be formed of a transparent or translucent polymer such as an epoxy material. In some embodiments the header 104 can be hollow. In other embodiments the header 104 can be filled with components and/or structural materials such as epoxy or another material such that it is non-hollow.

The IMD 100 can also include a chemical sensor 106 coupled to the implantable housing 102. Chemical sensor 106 can be configured to detect an ion concentration of a bodily fluid when implanted in the body. In some embodiments, the chemical sensor 106 can be configured to detect an ion selected from the group consisting of potassium, sodium, chloride, calcium, magnesium, lithium, hydronium, hydrogen phosphate, bicarbonate, and the like. Bodily fluids can include blood, interstitial fluid, serum, lymph, serous fluid, cerebrospinal fluid, and the like. In some embodiments chemical sensor 106 can be configured to detect one or more of an electrolyte, a protein, a sugar, a hormone, a peptide, an amino acid, and a metabolic product. However, many other analytes are also contemplated herein.

It will be appreciated that chemical sensor 106 can be positioned at any location along IMD 100, including a location along the implantable housing 102 and a location along the header 104. The IMD 100 can take on various dimensions. In a particular embodiment herein it can be approximately 2 to 3 inches in length, 0.4 to 0.6 inches wide, and 0.15 to 0.35 inches thick. However, in some embodiments, the IMD 100 can be about 0.25, 0.5, 1.0, 2.0, 3.0, 4.0, or 5.0 inches in length. In some embodiments the length can be in a range wherein any of the foregoing lengths can serve as the upper or lower bound of the range, provided that the upper bound is greater than the lower bound. In some embodiments, the IMD 100 can be about 0.25, 0.5, 0.75, 1.0, or 2.0 inches in width. In some embodiments the length can be in a range wherein any of the foregoing widths can serve as the upper or lower bound of the range, provided that the upper bound is greater than the lower bound. In some embodiments, the IMD 100 can be about 0.10, 0.25, 0.50, 0.75 or 1.0 inches thick. In some embodiments the thickness can be in a range wherein any of the foregoing thicknesses can serve as the upper or lower bound of the range, provided that the upper bound is greater than the lower bound.

In some embodiments, the chemical sensor 106 can be in the shape of a circle. The diameter of the chemical sensor 106 can be about 0.5 mm, 0.75 mm, 1.0 mm, 1.5 mm, 1.75 mm, 2.0 mm, 2.5 mm, 2.75 mm, 3.0 mm, 3.25 mm, 3.5 mm, 3.75 mm, 4.0 mm, 4.5 mm, or 5.0 mm. In some embodiments the diameter can be in a range wherein any of the foregoing diameters can serve as the upper or lower bound of the range, provided that the upper bound is greater than the lower bound. In some embodiments, the diameter of the chemical sensor 106 is greater than or equal to 1.5 mm. Though chemical sensor 106 is depicted in FIG. 1 in the shape of a circle, it will be appreciated that chemical sensor 106 can assume a variety of shapes, including but not limited to a square, a rectangle, a triangle, a trapezoid, an oval, and the like. It will also be appreciated that IMD 100 can include one or more chemical sensors that measure the same, or different analytes. In some embodiments, one or more chemical sensors can be arranged as an array in a variety of shapes, such as, for example, a grid, a circle, a mosaic, a geometric patter, or the like.

The height (depth) of the chemical sensor 106 can be about 0.1 mm, 0.2 mm, 0.3 mm, 0.4 mm, 0.5 mm, 0.75 mm, 1.0 mm, 1.5 mm, 1.75 mm, 2.0 mm, 2.5 mm, 2.75 mm, 3.0 mm, 3.25 mm, 3.5 mm, 3.75 mm, 4.0 mm, 4.5 mm, or 5.0 mm, 6 mm, 7 mm, 8 mm, 9 mm, or 10 mm. In some embodiments the height of the chemical sensor 106 can be in a range wherein any of the foregoing distances can serve as the upper or lower bound of the range, provided that the upper bound is greater than the lower bound.

Figure 2:
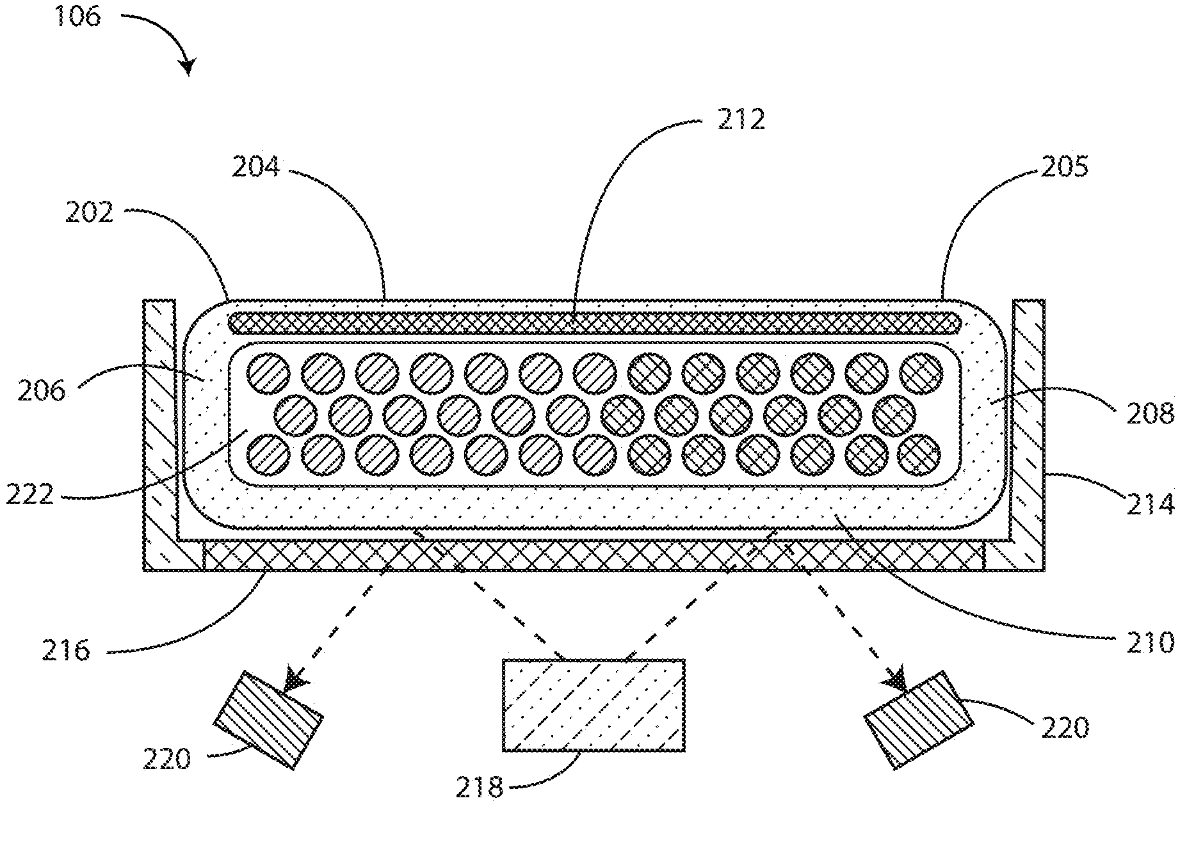
FIG. 2 is a cross-sectional view of a chemical sensor taken along line 2-2' of FIG. 1.
Figure 3:
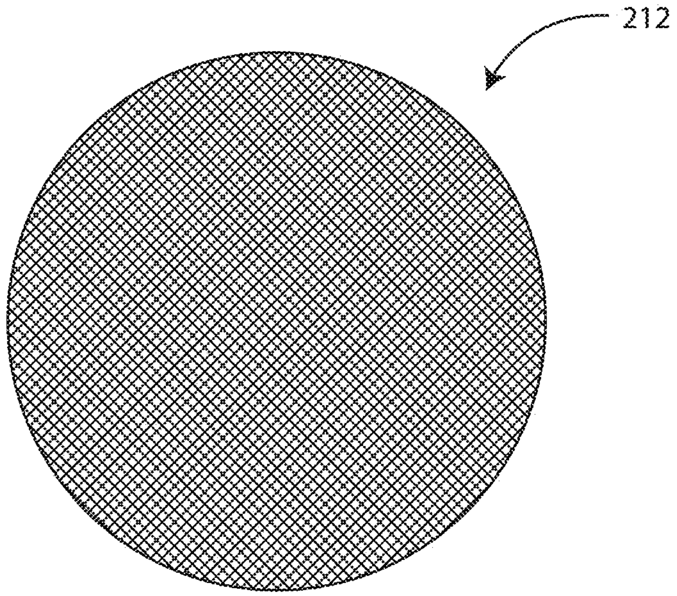
FIG. 3 is a schematic plan view of a structural reinforcing element in accordance with various embodiments herein.

Referring now to FIG. 2, a cross-sectional view of chemical sensor 106 along line 2-2' of FIG. 1 is shown. Chemical sensor 106 can include, but not be limited to, sensing element 202, optical excitation assembly 218, and optical detection assembly 220. FIG. 3 shows an optical chemical sensor. However, in other embodiments the chemical sensor can be a potentiometric chemical sensor.

The sensing element 202 can include an outer barrier layer 204 formed, in full or in part, from a permeable material, such as an ion permeable polymeric matrix material, and the like. Exemplary materials for the outer barrier layer 204 are described in greater detail below. Outer barrier layer 204 can form a top 205, a bottom 210, and opposed sides 206 and 208 to surround an interior volume 222 of sensing element 202. Bottom 210 and opposed sides 206 and 208 of outer barrier layer 204 will be discussed in more detail below in reference to FIGS. 3-5. Briefly, however, they can be formed of the same material as the top 205, or they can be formed from a different material. In some embodiments, at least the top 205 of outer barrier layer 204 can be permeable to sodium ions, potassium ions, hydronium ions, creatinine, urea, and the like. Outer barrier layer 204 can also include an active agent disposed therein including, but not limited to anti-inflammatory agents, angiogenic agents, and the like. Exemplary active agents are described in greater detail below.

It will be appreciated, however, that bottom 210 may or may not be a discrete layer. For example, in some embodiments, bottom 210 and a transparent member 216 within a recessed pan 214 of the implantable housing 102 may be combined with different material or combined as one layer with same type of material.

The outer barrier layer 204 can include a structural reinforcing element 212 disposed within, on or under the outer surface of the outer barrier layer 204. For example, the structural reinforcing element 212 can be disposed within, on top of, or beneath the outer barrier layer 204. In some embodiments, the structural reinforcing element 212 can be disposed within, on or under the exterior surface of opposed sides 206 and 208. In yet other embodiments, structural reinforcing element 212 can be disposed within, on or under the outer surface of bottom 210 of the outer barrier layer 204. In still other embodiments, the structural reinforcing element 212 can be disposed within, on or under the outer surface of the entire outer barrier layer 204. The structural reinforcing element will be further discussed in reference to FIGS. 3-5 below. It will be appreciated that the structural reinforcing elements embodied herein can take on many shapes and forms in accordance with additional embodiments herein.

The structural reinforcing elements can come in various shapes and sizes. In some embodiments, the structural reinforcing elements can be columnar, pyramidal, frustopyramidal, conical, frustoconical, cylindrical, rectangular, and the like. In some embodiments, the base of the structural reinforcing element can have a greater width than the top of the structural reinforcing element. In some embodiments, the top of the structural reinforcing element can have a greater width than the bottom of the structural reinforcing element. In some embodiments, the top and the bottom of the structural reinforcing element can have the same width. The height of the structural reinforcing elements can be about 0.1 mm, 0.2 mm, 0.3 mm, 0.4 mm, 0.5 mm, 0.75 mm, 1.0 mm, 1.5 mm, 1.75 mm, 2.0 mm, 2.5 mm, 2.75 mm, 3.0 mm, 3.25 mm, 3.5 mm, 3.75 mm, 4.0 mm, 4.5 mm, or 5.0 mm, 6 mm, 7 mm, 8 mm, 9 mm, or 10 mm. In some embodiments the height of the structural reinforcing elements can be in a range wherein any of the foregoing diameters can serve as the upper or lower bound of the range, provided that the upper bound is greater than the lower bound.

The structural reinforcing elements can be positioned in various places within the sensing element. In some embodiments, there can be multiple structural reinforcing elements and they can be spaced out across the sensing element (such as spaced out across the width of the chemical sensor along X and/or Y axes, wherein the depth of the chemical sensor would be the Z axis). In some embodiments, multiple structural reinforcing elements can be evenly spaced out. In some embodiments, multiple structural reinforcing elements can spaced from each other, but with a bias toward the middle of the diameter of the chemical sensor, such that a central portion (such as a central 50% of the overall diameter) has a higher density of structural reinforcing elements.

Materials suitable for forming the structural reinforcing elements discussed herein can include, but not be limited to, porous rigid polymers, porous rigid ceramics, polyester, polyurethane, polyethylene, polypropylene, nylon, sintered titanium, deep reactive-ion etched silicon, sintered stainless steel, sintered silica, liquid crystal, glass, silica-containing glass, borosilicate glass such as but not limited to VYCOR®, or mixtures or derivatives thereof. Structural reinforcing elements will be discussed in more detail below.

The implantable housing 102 can include a recessed pan 214 into which the sensing element 202 fits. In some embodiments, the top of the recessed pan 214 can be substantially flush with the top of the sensing element 202.

In some embodiments, implantable housing 102 can define an aperture occluded by a transparent member 216. The transparent member 216 can be a glass (including but not limited to borosilicate glasses), a polymer or other transparent material. The aperture can be disposed at the bottom of the recessed pan 214. The aperture can provide an interface allowing for optical communication between sensing element 202 and the optical excitation 218 and optical detection 220 assemblies. In some embodiments, the bottom 210 of the outer barrier layer 204 can be combined with the transparent member 216. Bottom 210 and transparent member 216 may be combined with different material or combined as one layer with same type of material.

It will be appreciated that outer barrier layer 204, or portions thereof such as the bottom 210, can be made from a transparent polymer matrix material to allow for optical communication between the sensing element 202 and optical excitation 218 and optical detection 220 assemblies.

The optical excitation assembly 218 can be configured to illuminate the sensing element 202. Optical excitation assembly 218 can include a light source such as a light emitting diode (LED), vertical-cavity surface-emitting lasers (VCSELs), electroluminescent (EL) devices, and the like. Optical detection assembly 220 can include a component selected from the group consisting of a photodiode, a phototransistor, a charge-coupled device (CCD), a junction field effect transistor (JFET) optical sensor, a complementary metal-oxide semiconductor (CMOS) optical sensor, an integrated photo detector integrated circuit, a light to voltage converter, and the like. Optical excitation 218 and optical detection 220 assemblies are discussed in further detail below.

Referring now to FIG. 3, a schematic plan view is shown of a structural reinforcing element 212 in accordance with various embodiments herein. The structural reinforcing element 212 can take on many different shapes including but not limited to a square, a rectangle, a triangle, a trapezoid, an oval, and the like.

Figure 4:
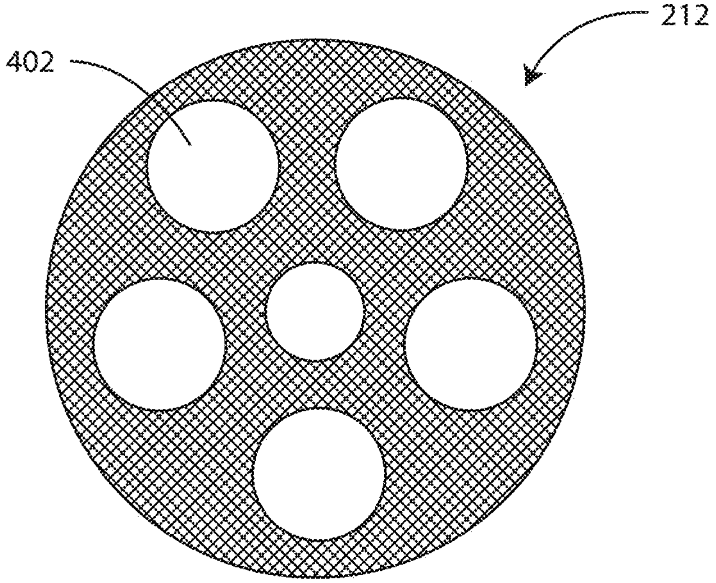
FIG. 4 is a schematic plan view of a structural reinforcing element in accordance with various embodiments herein.

In the view of FIG. 3, the structural reinforcing element 212 is solid, but porous. However, it will be appreciated that in some embodiments, the structural reinforcing element 212 can be formed of a non-porous material. Further, in some embodiments, the structural reinforcing element can include one or more apertures disposed therein. Referring now to FIG. 4 a schematic plan view is shown of a structural reinforcing element 212 in accordance with various embodiments herein. As can be seen, the structural reinforcing element 212 includes apertures 402.

Figure 5:
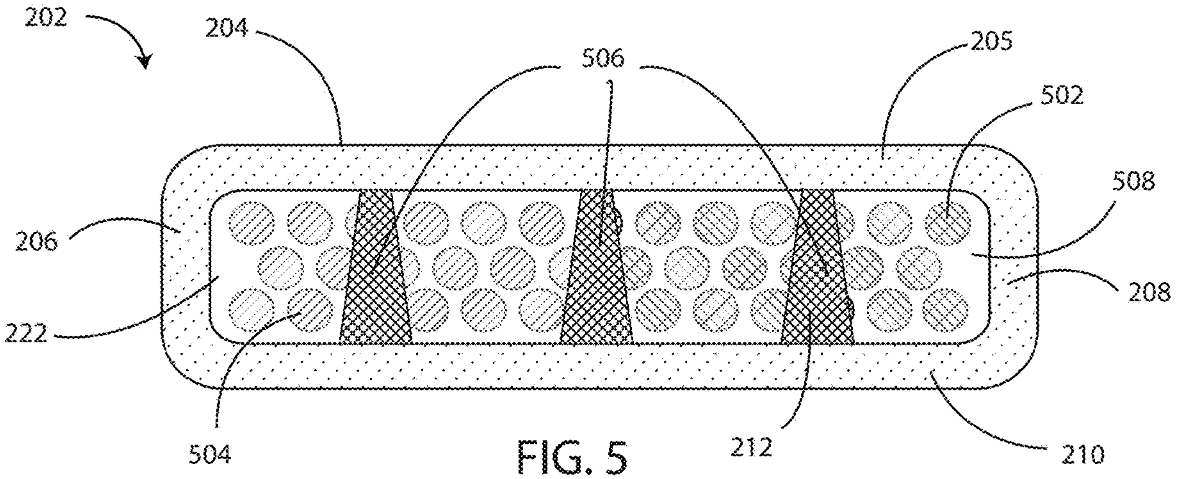
FIG. 5 is a cross-sectional view of a chemical sensor in accordance with additional embodiments herein.
Figure 6:
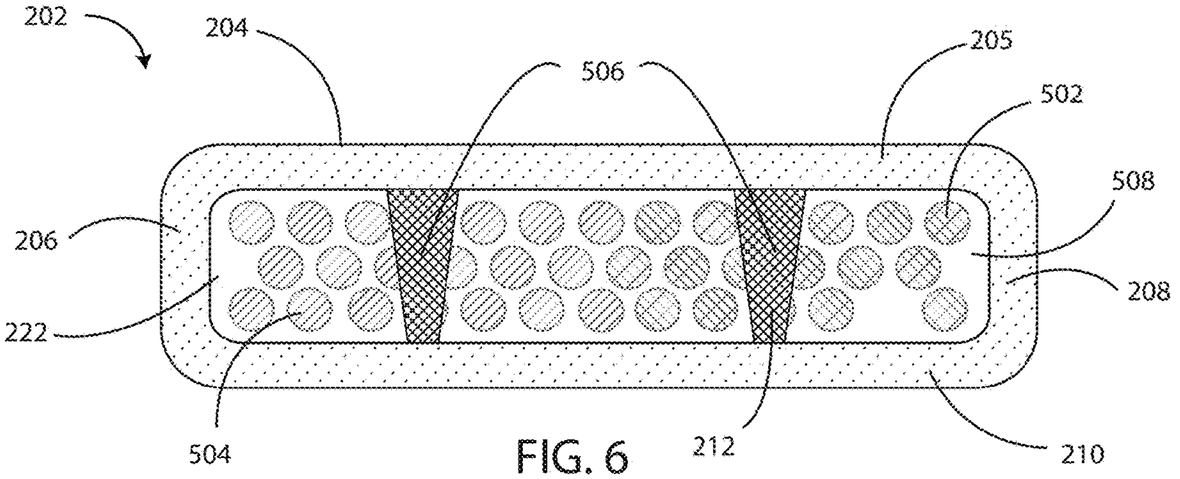
FIG. 6 is a cross-sectional view of a chemical sensor in accordance with additional embodiments herein.
Figure 7:
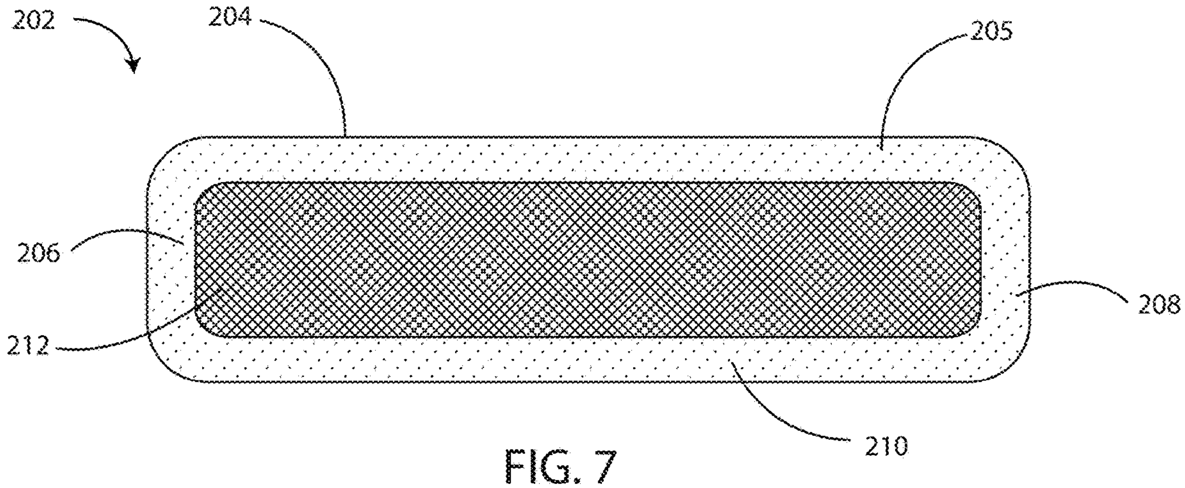
FIG. 7 is a cross-sectional view of a chemical sensor in accordance with additional embodiments herein.

Referring now to FIGS. 5-7, sensing element 202 is shown in accordance with various embodiments herein. As discussed above with reference to FIG. 2, sensing element 202 can include an outer barrier layer 204. Outer barrier layer 204 can form a top 205, a bottom 210, and opposed sides 206 and 208 to surround an interior volume 222 of sensing element 202. Outer barrier layer 204 can also include a structural reinforcing element 212.

For example, FIG. 5 shows a sensing element 202 having an outer barrier layer 204, the outer barrier layer including a top 205, a bottom 210, and opposing sides 206 and 208, the entirety of which can be formed from a material permeable to sodium ions, potassium ions, and hydronium ions, and the like. Materials suitable for use in the outer barrier layer 204 are discussed further below.

The sensing element 202 can include one or more intramural struts 306 spanning a distance between the top 205 and the bottom 210 of the outer barrier layer 204. The one or more intramural struts 506 can include a structural reinforcing element 212 disposed within, on or under the outer surface of the intramural struts 506. Materials suitable for forming the structural reinforcing element 212 of the one or more intramural struts 506 can include, but not be limited to rigid porous polymers, rigid porous ceramics, polyester, polyurethane, polyethylene, polypropylene, nylon, sintered titanium, deep reactive-ion etched silicon, sintered stainless steel, sintered silica, liquid crystal, glass, borosilicate glass, or mixtures or derivatives thereof.

In some embodiments, the intramural struts 306 can have a larger size or diameter on the side that contacts the bottom 210 in comparison to the size of the intramural struts that contacts the top 205. However, the reverse may also be true, such as shown in FIG. 6 described below. In some embodiments, the intramural struts 306 can be circular, oval, square, or polygonal in cross-section. The length of the struts can depend on the size of the sensing element, but in some embodiments can be 0.1 mm, 0.2 mm, 0.3 mm, 0.4 mm, 0.5 mm, 0.6 mm, 0.7 mm, 0.8 mm, 0.9 mm, 1 mm, 2 mm, 3 mm, 4 mm, 5 mm, 7 mm, 9 mm, 11 mm, 13 mm, 15 mm, 20 mm, or 30 mm; or can fall within a range between any of the foregoing distances. The number of struts can vary. The number of struts used can be 1, 2, 3, 4, 5, 7, 9, 11, 13, 15, 20, 25, 30, 40, 50, 60, 80, 100 or more. In some embodiments, the number of struts can fall within a range between any of the foregoing.

The sensing element(s) 202 embodied herein can include an interior volume 222 and can also include disposed therein various indicator beads for detecting an ion concentration of a bodily fluid when implanted in the body. For example, FIG. 5 shows a first indicator bead 502 and a second indicator bead 504. The first and second indicator beads 502 and 504 can include a polymeric support material and one or more ion selective sensors as described more fully below. Physiological analytes such as potassium ion, sodium ion, hydronium ion, and the like, can diffuse through the top 205 of the outer barrier layer 204, and where present, the structural reinforcing element 212, and onto and/or into first and second indicator beads 502 and 504 where they can bind with the ion selective sensors to produce a fluorimetric or colorimetric response.

In some embodiments, the first indicator beads 502 can be segregated to one side of the interior volume 222, with or without an interior divider. In some embodiments, the second indicator beads 504 can be segregated to a different side of the interior volume than the first indicator beads 502. In some embodiments, the first indicator beads 502 and second indicator beads 504 can be designed to detect the same analyte. In some embodiments, the first indicator beads 502 and second indicator beads 504 can be designed to detect the different analytes. In some embodiments the first indicator beads 502 and the second indicator beads 504 can be separated out by having two individual outer barrier layers 204. For example, instead of a single outer barrier layer 204, there can be two discrete outer barrier layers 204 with each surrounding a separate set of indicator beads. In various embodiments, the two sets of beads can be spaced out by a certain distance, such as at least about 0.1, 0.2, 0.3, 0.4, 0.5, 1, 2, 3, 5, 10 or 15 millimeters and less than 100, 70, 50, 40, 30, or 20 millimeters.

Beyond diffusion through the top 205, in some embodiments additional diffusion of physiological analytes is also possible through bottom 210, opposing sides 206 and 208, and, where present, the structural reinforcing element 212.

Figure 8:
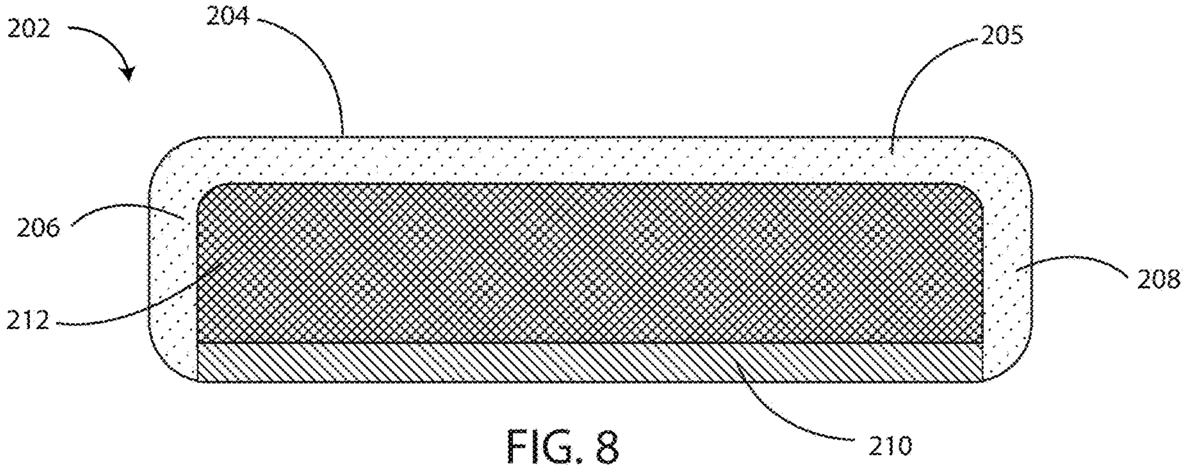
FIG. 8 is a cross-sectional view of a chemical sensor in accordance with additional embodiments herein.

While FIG. 5 shows discrete indicator beads, it will be appreciated that the indicator components can also exist in other forms such as a single larger combined mass, an infusion, or the like, as will be discussed with respect to FIGS. 7 and 8.

In some embodiments, the sensing element(s) 202 embodied herein can include an aqueous solution 508 disposed within the interior volume 222. In some embodiments, the aqueous solution 508 can include potassium ions at a concentration of about 3.0 to about 6.0 mmol/L. In some embodiments, the aqueous solution 508 can include potassium ions at a concentration of about 1.0, 2.0, 3.0, 4.0, 5.0, 6.0, 7.0, or 8.0 mmol/L. In some embodiments, the concentration of potassium ions in the aqueous solution 508 can be in a range between any of the foregoing multiples provided that the upper bound of the range is greater than the lower bound of the range. In some embodiments, the aqueous solution 508 can surround the exterior of sensing element 202 during packaging and prior to use, as discussed below in reference to FIG. 10.

In FIGS. 5 and 6, sensing element 202 is shown having an outer barrier layer 204, the outer barrier layer including a top 205, a bottom 210, and opposing sides 206 and 208, the entirety of which can be formed from a polymeric matrix permeable to sodium ions, potassium ions, and hydronium ions, and the like. Permeable materials suitable for use in the outer barrier layer 204 are discussed further below.

FIG. 5 shows a structural reinforcing element 212 disposed within the interior volume 222 of sensing element 202. In the embodiment shown in FIG. 6, the structural reinforcing element 212 can be created from a porous material. In some embodiments, the structural reinforcing element 212 can fill at least 5%, 10%, 15%, 20%, 25%, 30%, 40%, or 50% of the interior volume 222 of sensing element 202. It will be appreciated that the structural reinforcing element 212 can fill an interior volume falling within a range, wherein any of the forgoing percentages can serve as the lower or upper bound of the range, provided that the lower bound of the range is a value less than the upper bound of the range. In some embodiments, the structural reinforcing element 212 disposed within interior volume 222 can be infused with one or more ion selective sensors, which are described more fully below.

FIG. 6 shows a structural reinforcing element 212 disposed within the interior volume 222 of sensing element 202. In the embodiment shown in FIG. 6, the structural reinforcing element 212 can be created from a porous material. In some embodiments, the structural reinforcing element 212 can fill at least 5%, 10%, 15%, 20%, 25%, 30%, 40%, or 50% of the interior volume 222 of sensing element 202. In some embodiments, the structural reinforcing element 212 disposed within interior volume 222 can be infused with one or more ion selective sensors, which are described more fully below. The structural reinforcing element 212 can include one or more intramural struts 506.

It will be appreciated that some portions of the outer barrier layer 204 can be formed of a different material, while in other embodiments the entire outer barrier layer 204 can be formed of the same material. FIG. 7, shows a sensing element 202 having an outer barrier layer 204 where the top 205, and opposing sides 206 and 208 are formed from the same material that is permeable to sodium ions, potassium ions, and hydronium ions, and the like. The bottom 210 is shown having a different material composition. It will be appreciated that bottom 210 of outer barrier layer 204 can be formed of a transparent material to couple the sensing element 202 to the optical excitation 218 and optical detection 220 assemblies. Coupling the sensing element 202 to the optical excitation 218 and optical detection 220 assemblies can facilitate optical communication between the two structures.

However, in some embodiments, the bottom can be formed from a different material than the outer barrier layer. Referring now to FIG. 8, another cross-sectional view of a chemical sensor is shown in accordance with some embodiments. In some embodiments, the bottom 210 can be formed from a glass, such as a borosilicate glass. In some embodiments, the bottom 210 can be formed from transparent polymeric materials. In some embodiments, bottom 210 can be fused to an implantable housing at the interface with a transparent member, as discussed above.

Figure 9:
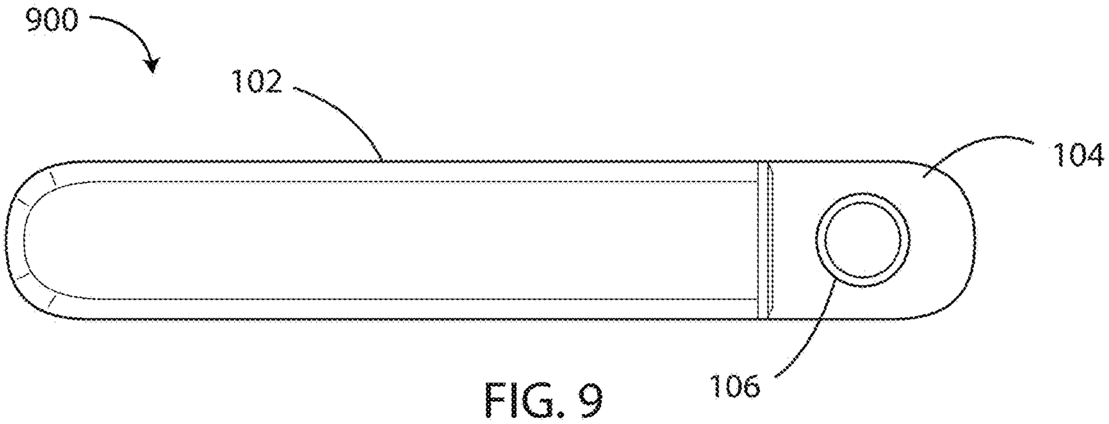
FIG. 9 is a schematic top view of an implantable medical device in accordance with additional embodiments herein.

Referring now to FIG. 9, an implantable medical device 900 is shown in accordance with the embodiments herein. Implantable medical device 900 can include an implantable housing 102 coupled to a header 104. The chemical sensor 106 is shown coupled to the header 104. It will be appreciated that more than one chemical sensor can be included in the header 104 of medical device 900.

Figure 10:
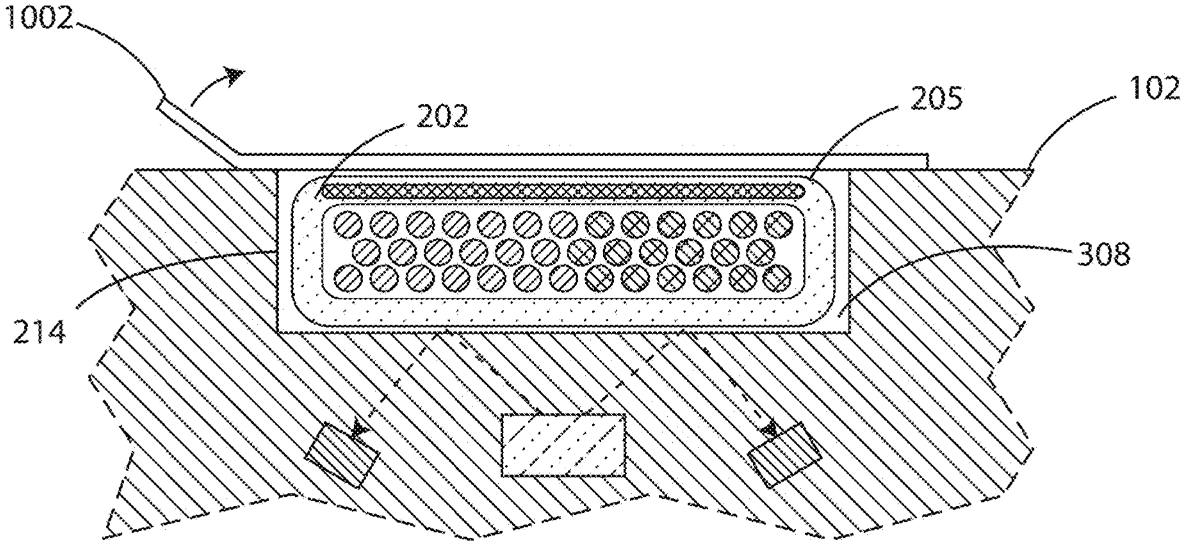
FIG. 10 is a schematic cross-sectional view of a sensing element in accordance with additional embodiments herein.

In some embodiments, it may be desirable to ship the chemical sensor and/or medical device with the sensor pre-wetted (e.g., bathed in an aqueous solution). Referring now to FIG. 10, an embodiment of chemical sensor 106 is shown having a seal 1002 over the top 205 of sensing element 202. Seal 1002 can provide a tight seal between the external environment and the chemical sensor 106 when packaged. For example, seal 1002 can provide an effective barrier to keep aqueous solution 308 within recessed pan 214 such that the sensing element 202 can be constantly bathed in aqueous solution 308 prior to implant.

In some embodiments, the aqueous solution 308 present in recessed pan 214 can also include potassium ions at a concentration of about 3.0 to about 6.0 mmol/L. In some embodiments, the aqueous solution 308 can include potassium ions at a concentration of about 1.0, 2.0, 3.0, 4.0, 5.0, 6.0, 7.0, or 8.0 mmol/L. In some embodiments, the concentration of potassium ions in the aqueous solution 308 can be in a range between any of the foregoing amounts provided that the upper bound of the range is greater than the lower bound of the range.

Seal 1002 can be removed from the chemical sensor 106 by a medical professional just prior to implantation. In some embodiments, seal 1002 can be non-porous to the passage of aqueous solutions. In some embodiments, seal 1002 can be made from a polymer such as polyethylene terephthalate (PET), polytetrafluoroethylene (PTFE), polyethylene, polystyrene, and the like. In some embodiments, the seal 1002 can be made from a foil, such as a metal foil. In some embodiments, the seal 1002 can be made from a radiopaque material.

Figure 11:
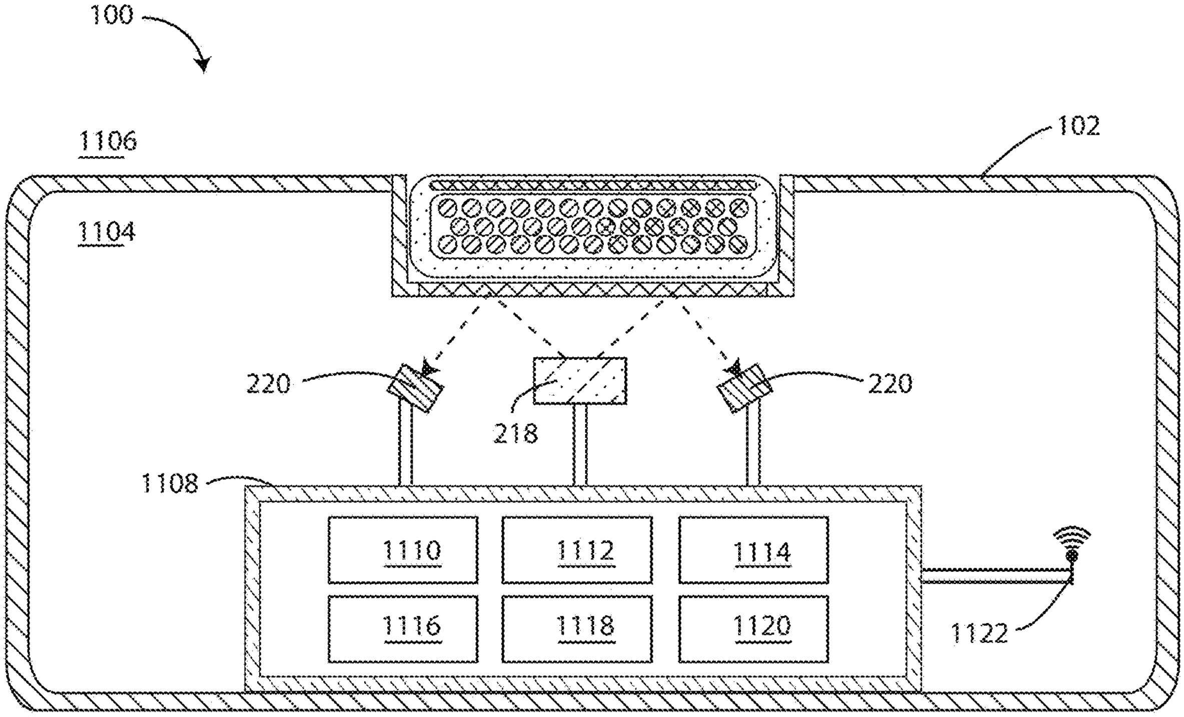
FIG. 11 is a schematic cross-sectional view of an implantable medical device in accordance with various embodiments herein.

Referring now to FIG. 11, a schematic cross-sectional view of IMD 100 is shown in accordance with various embodiments herein. The IMD 100 can include implantable housing 102. The implantable housing 102 of IMD 100 can include various materials such as metals, polymers, ceramics, and the like. In some embodiments, the implantable housing 102 can be a single integrated unit. In other embodiments, the implantable housing 102 can include implantable housing 102 and epoxy header 104, as discussed above. In some embodiments, the implantable housing 102, or one or more portions thereof, can be formed of titanium. In some embodiments, one or more segments of the implantable housing 102 can be hermetically sealed.

Implantable housing 102 can define an interior volume 804 that in some embodiments is hermetically sealed off from the area 1106 outside of IMD 100. The IMD 100 can include circuitry 1108. Circuitry 1108 can include various components, such as components 1110, 1112, 1114, 1116, 1118, and 1120. In some embodiments, these components can be integrated and in other embodiments these components can be separate. In some embodiments, the components can include one or more of a microprocessor, memory circuitry (such as random access memory (RAM) and/or read only memory (ROM)), recorder circuitry, telemetry circuitry, chemical sensor interface circuitry, power supply circuitry (which can include one or more batteries), normalization circuitry, chemical sensor control circuitry, and the like. In some embodiments recorder circuitry can record the data produced by the chemical sensor and record time stamps regarding the same. In some embodiments, the circuitry can be hardwired to execute various functions, while in other embodiments the circuitry can be implemented as instructions executing on a microprocessor or other computation device.

A telemetry interface 1122 can be provided for communicating with external devices such as a programmer, a home-based unit, and/or a mobile unit (e.g., a cellular phone, portable computer, etc.). In some embodiments telemetry interface 1122 can be provided for communicating with implanted devices such as a therapy delivery device (e.g. a pacemaker, cardioverter-defibrillator) or monitoring-only device (e.g. an implantable loop recorder). In some embodiments, the circuitry can be implemented remotely, via either near-field, far-field, conducted, intra-body or extracorporeal communication, from instructions executing on any of the external or the implanted devices, etc. In some embodiments, the telemetry interface 1122 can be located within implantable housing 102. In some embodiments, the telemetry interface 1122 can be located in header 104.

The optical excitation 218 and optical detection 220 assemblies of the chemical sensor 106 can be in electrical communication with the circuitry 1108 within the interior volume 1104. In some embodiments, the control circuitry 1108 is configured to selectively activate the optical excitation 218 and optical detection 220 assemblies of the chemical sensor 106.

Figure 12:
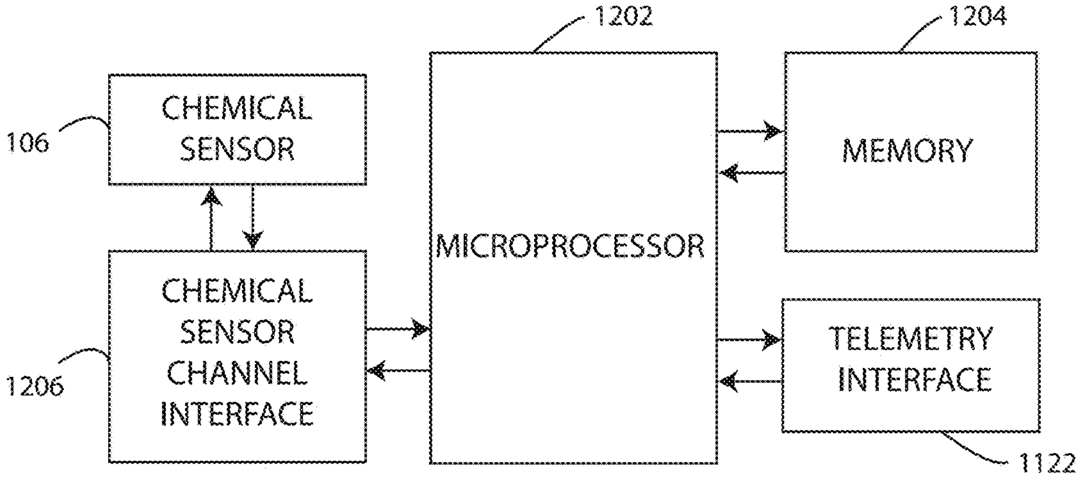
FIG. 12 is a schematic diagram of components of an implantable medical device in accordance with various embodiments herein.

Referring now to FIG. 12, a schematic diagram of components of IMD 100 in accordance with various embodiments herein. It will be appreciated that some embodiments can include additional elements beyond those shown in FIG. 12. In addition, some embodiments may lack some elements shown in FIG. 12. IMD 100 can gather information through one or more sensing channels. A microprocessor 1202 can communicate with a memory 1204 via a bidirectional data bus. The memory 1204 can include read only memory (ROM) or random access memory (RAM) for program storage and RAM for data storage, or any combination thereof. The implantable medical device can also include one or more chemical sensors 106 and one or more chemical sensor channel interfaces 1206 which can communicate with a port of microprocessor 1202. The chemical sensor channel interface 1206 can include various components such as analog-to-digital converters for digitizing signal inputs, sensing amplifiers, registers which can be written to by the control circuitry in order to adjust the gain and threshold values for the sensing amplifiers, source drivers, modulators, demodulators, multiplexers, and the like. A telemetry interface 1122 is also provided for communicating with external devices such as a programmer, a home-based unit, and/or a mobile unit (e.g., a cellular phone, portable computer, etc.), implanted devices such as a pacemaker, cardioverter-defibrillator, loop recorder, and the like.

Outer Barrier Layer

As referenced above, the outer barrier layer of the sensing element can be formed of a permeable material. In some embodiments, the outer barrier layer can be formed from an ion-permeable polymeric matrix material. Suitable polymers for use as the ion-permeable polymeric matrix material can include, but are not limited to polymers forming a hydrogel. Hydrogels herein can include homopolymeric hydrogels, copolymeric hydrogels, and multipolymer interpenetrating polymeric hydrogels. Hydrogels herein can specifically include nonionic hydrogels.

In some embodiments, hydrogels herein can be prepared from polymerization of various monomers or macromers including one or more of poly 2-hydroxyethyl methacrylate (polyHEMA), 2-hydroxypropyl methacrylate (HPMA), acrylamide, acrylic acid, N-isopropylacrylamide (NIPAm), methoxyl polyethylene glycol monoacrylate (PEGMA), and the like. In some embodiments, polymers can include, but are not limited to polyhydroxyethyl methacrylate (HEMA), cellulose, polyvinyl alcohol, polyacrylate, dextran, polyacrylamides, polyhydroxyalkyl acrylates, polyvinyl pyrrolidones, and mixtures and copolymers thereof. In some embodiments, suitable polymers for use with the ion-permeable polymeric matrix described herein include those that are transparent. In yet other embodiments, the outer barrier layer can be formed from porous materials such as, agarose, alginates, collagen, polyethylene glycol (PEG), gelatin, glass, borosilicate glass, or mixtures or derivatives thereof. In some embodiments, the outer barrier layer is formed from glass. In some embodiments, the outer barrier layer is formed from borosilicate glass.

Structural Reinforcing Element

As discussed above, the outer barrier layer of the sensing element can include a structural reinforcing element disposed within the outer barrier layer. In other embodiments, the structural reinforcing element can be disposed on the outer or inner surfaces of the outer barrier layer. In some embodiments, the structural reinforcing element can be formed from an ion-permeable material. In other embodiments, the structural reinforcing element can be formed from a non-permeable material.

Materials suitable for use with the structural reinforcing elements herein can include polyesters, such as polychtylene terephthalate (e.g., Dacron®); polyurethanes, including but not limited to Tecothane® aromatic polyether-based thermoplastic polyurethanes (TPUs); polyethylene; polypropylene; nylon; silk; polymethylmethacrylate (PMMA); sintered titanium; deep reactive-ion etched silicon; sintered stainless steel; sintered silica; liquid crystal; alumina; ceramic; glass; borosilicate glass; and the like.

In some embodiments, the structural reinforcing element can exhibit a stiffness greater than the material of the outer barrier. In some embodiments, the structural reinforcing element can be about 10, 20, 30, 40, 50, 60, 80, 100, 150, 200, 300, 400, 500, 600, 700, 800, 900, 1000, 1500, 2000, or 2500 percent stiffer than the outer barrier layer material. In some embodiments, the structural reinforcing element can greater than 3000 percent stiffer than the outer barrier layer material.

In some embodiments, the structural reinforcing element can exhibit rigidity greater than the material of the outer barrier. In some embodiments, the structural reinforcing element can be about 10, 20, 30, 40, 50, 60, 80, 100, 150, 200, 300, 400, 500, 600, 700, 800, 900, 1000, 1500, 2000, or 2500 percent more rigid than the outer barrier layer material.

In some embodiments, the structural reinforcing element can exhibit greater tensile strength than the material of the outer barrier. In some embodiments, the structural reinforcing element can exhibit about 10, 20, 30, 40, 50, 60, 80, 100, 150, 200, 300, 400, 500, 600, 700, 800, 900, 1000, 1500, 2000, or 2500 percent more tensile strength than the outer barrier layer material.

In some embodiments, the structural reinforcing element can include a woven material. In some embodiments, the structural reinforcing element can include a woven material made from an ion-permeable polymeric material. In some embodiments, the structural reinforcing element can include a woven material made from a non-permeable material. In some embodiments, the woven material can include a uniform weave pattern of fibers throughout the entirety of the structural reinforcing element. In other embodiments, the woven material can include a non-uniform weave pattern of fibers throughout the entirety of the structural reinforcing element. In some embodiments, the woven material can include oriented weave patterns. In other embodiments, the structural reinforcing element can include a non-woven material having a non-uniform weave pattern of fibers throughout the entirety of the structural reinforcing element. An example of a non-woven material is Tyvek®, which is made from high-density polyethylene fibers. In some embodiments, the structural reinforcing element can include an electrospun polymeric material. In some embodiments, the electrospun polymeric material can include a randomly woven polymeric material.

In yet other embodiments, the structural reinforcing element can be formed into a one-piece molded unit that can be infused with one or more ion selective sensors.

Ion Selective Sensors

In accordance with the embodiments herein, sensing elements 202 can include one or more ion selective sensors included within one or more types of indicator beads, or infused within the structural reinforcing elements as described herein. Ion selective sensors may either rely on surface phenomena or on concentration changes inside the bulk of a phase. Ion selective sensors can include optical sensors, including both non-carrier optical sensors and carrier-based optical sensors, and ion-selective electrodes (ISEs). In some embodiments, the ion selective sensor is fluorimetric, and can include a complexing moiety and a fluorescing moiety. Fluorimetric ion selective sensors can exhibit differential fluorescent intensity based upon the complexing of an analyte to a complexing moiety. In some embodiments, the ion selective sensor can be colorimetric, and can include a complexing moiety and a colorimetric moiety. Colorimetric ion selective sensors can exhibit differential light absorbance based upon the complexing of an analyte to a complexing moiety.

In some embodiments, the ion selective sensor comprises a non-carrier or carrier-based fluorescent or colorimetric ionophoric composition that comprises a complexing moiety for reversibly binding an ion to be analyzed, and a fluorescing or colorimetric moiety that changes its optical properties as the complexing agent binds or releases the ion. The complexing agents of the invention can optionally be appended with one or more organic substituents chosen to confer desired properties useful in formulating the ion sensing composition. By way of example, the substituents can be selected to stabilize the complexing agent with respect to leaching into the solution to be sensed, for example, by incorporating a hydrophobic or polymeric tail or by providing a means for covalent attachment of the complexing agent to a polymer support within the ion selective sensor.

In some embodiments, the sensing element can include ion selective sensors such as an ionophore or a fluoroionophore. Suitable ionophores for use with the embodiments herein can include, but not be limited to, sodium specific ionophores, potassium specific ionophores, calcium specific ionophores, magnesium specific ionophores, and lithium specific ionophores. Suitable fluoroionophores for use with the embodiments herein can include, but not be limited to, lithium specific fluoroionophores, sodium specific fluoroionophores, and potassium specific fluoroionophores.

Exemplary ion selective sensors and methods for their use are disclosed in commonly assigned U.S. Pat. No. 7,809,441, the contents of which is herein incorporated by reference in its entirety.

Optical Excitation and Detection Assemblies

In some embodiments, the optical excitation assembly 218 can include solid state light sources such as GaAs, GaAlAs, GaAlAsP, GaAlP, GaAsP, GaP, GaN, InGaAlP, InGaN, ZnSe, or SiC light emitting diodes or laser diodes that excite the sensing element(s) 202 at or near the wavelength of maximum absorption for a time sufficient to emit a return signal. However, it will be understood that in some embodiments the wavelength of maximum absorption/reflection varies as a function of concentration in the colorimetric sensor.

In some embodiments, the optical excitation assembly 218 can include other light emitting components including incandescent components. In some embodiments, the optical excitation assembly 218 can include a waveguide. The optical excitation assembly 218 can also include one or more bandpass filters, high pass filter, low pass filter, antireflection elements, and/or focusing optics.

In some embodiments, the optical excitation assembly 218 can include a plurality of LEDs with bandpass filters, each of the LED-filter combinations emitting at a different center frequency. According to various embodiments, the LEDs can operate at different center-frequencies, sequentially turning on and off during a measurement, illuminating the sensing element 202. As multiple different center-frequency measurements are made sequentially, a single unfiltered detector can be used in some embodiments. However, in some embodiments, a polychromatic source can be used with multiple detectors that are each bandpass filtered to a particular center frequency.

The sensing element 202 can include one or more types of indicator beads having embedded therein various types of ion selective sensors, described below. Physiological analytes of interest can diffuse into and out of the sensing element 202 and bind with an ion selective sensor to result in a fluorimetric or colorimetric response. Reference analytes can similarly diffuse into and out of the sensing element 202 and serve as a control sample. Exemplary ion selective sensors are described more fully below.

The optical detection assembly 220 can be configured to receive light from the sensing element 202. In an embodiment, the optical detection assembly 220 can include a component to receive light. By way of example, in some embodiments, the optical detection assembly 220 can include a charge-coupled device (CCD). In other embodiments, the optical detection assembly 220 can include a photodiode, a junction field effect transistor (JFET) type optical sensor, or a complementary metal-oxide semiconductor (CMOS) type optical sensor. In some embodiments, the optical detection assembly 220 can include an array of optical sensing components. In some embodiments, the optical detection assembly 220 can include a waveguide. The optical detection assembly 220 can also include one or more bandpass filters and/or focusing optics. In some embodiments, the optical detection assembly 220 can include one or more photodiode detectors, each with an optical bandpass filter tuned to a specific wavelength range.

The optical excitation and detection assemblies, 218 and 220, respectively, can be integrated using bifurcated fiber-optics that direct excitation light from a light source to one or more sensing elements 202, or simultaneously to sensing element(s) 202 and a reference channel. Return fibers can direct emission signals from the sensing element(s) 202 and the reference channels to one or more optical detection assemblies 220 for analysis by a processor, such as a microprocessor. In some embodiments, the optical excitation and detection assemblies are integrated using a beam-splitter assembly and focusing optical lenses that direct excitation light from a light source to the sensing element and direct emitted or reflected light from the sensing element to an optical detector for analysis by a processor.

Active Agents

Various embodiments herein can include an active agent disposed within the outer barrier layer. The active agent can be any drug or bioactive agent which can serve as a useful therapeutic, prophylactic, or even diagnostic agent when released into the patient. Exemplary bioactive agents include, but are not limited to, the following: an anti-inflammatory; anti-proliferative; anti-arrhythmic; anti-migratory; anti-neoplastic; antibiotic; anti-restenotic; anti-coagulation; anti-infectives; anti-oxidants; anti-macrophagic agents (e.g., bisphosphonates); anti-clotting (e.g., heparin, coumadin, aspirin); anti-thrombogenic; immunosuppressive agents; an agent that promotes healing; steroids (e.g., a glucocorticosteroid)); and combinations thereof.

Suitable active agents for use with the embodiments herein can specifically include, but are not limited to anti-inflammatory agents. In some embodiments, suitable anti-inflammatory agents can include steroids generally and, in specific, corticosteroids. In some embodiments, the anti-inflammatory agent can include ketorolac, dexamethasone, hydrocortisone, prednisolone, methylprednisolone, indomethacin, diclofenac, ketoprofen, piroxicam, metamizol magnesium and the like. In some embodiments, anti-inflammatory agents can be configured to be eluted shortly after implantation of the device.

In some embodiments, suitable active agents can also include angiogenic agents, to promote the in-growth of capillaries. In some embodiments, angiogenic agents can be configured to be eluted at a later time (e.g., following elution of an anti-inflammatory at an earlier point in time) to promote the ingrowth of capillaries to the chemical sensor.

In some embodiments, suitable angiogenic agents can include growth factors such as vascular endothelial growth factor (VEGF), fibroblast growth factor (FGF), platelet-derived growth factor (PDGF), and the like. In some embodiments, the additional active agents can include immobilized heparin to prevent blot clot formation.

Active agents herein can be in various forms including in a solution, as a suspension, as a particulate, or the like.

The embodiments described herein are not intended to be exhaustive or to limit the invention to the precise forms disclosed in the following detailed description. Rather, the embodiments are chosen and described so that others skilled in the art can appreciate and understand the principles and practices. Aspects have been described with reference to various specific and preferred embodiments and techniques. However, it should be understood that many variations and modifications may be made while remaining within the spirit and scope herein.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference. Nothing herein is to be construed as an admission that the inventors are not entitled to antedate any publication and/or patent, including any publication and/or patent cited herein.

The invention claimed is:

1. An implantable medical device comprising:
- a chemical sensor configured to detect an ion concentration in a bodily fluid, the chemical sensor comprising:
  - a sensing element, the sensing element comprising
    - a barrier layer forming a top wall, a bottom wall, and opposed side walls of the sensing element, the barrier layer comprising a hydrogel;
    - an interior volume comprising a plurality of indicator beads, wherein the interior volume is disposed between the top wall, the bottom wall, and the opposed side walls; and
    - a structural reinforcing element, wherein the structural reinforcing element comprises a different material than the barrier layer and exhibits rigidity greater than the material of the barrier layer;
  - wherein the barrier layer fully encapsulates all sides of the structural reinforcing element and all sides of the interior volume.

2. The implantable medical device of claim 1, the structural reinforcing element comprising polyester, polyurethane, polyethylene, polypropylene, nylon, sintered titanium, deep reactive-ion etched silicon, sintered stainless steel, sintered silica, liquid crystal, glass, borosilicate glass, or mixtures or derivatives thereof.

3. The implantable medical device of claim 1, the structural reinforcing element selected from the group comprising a woven material, a non-woven material, electrospun material, and randomly woven material.

4. The implantable medical device of claim 1, the chemical sensor further comprising one or more intramural struts spanning a distance between the top wall and the bottom wall of the barrier layer.

5. The implantable medical device of claim 4, the one or more intramural struts comprising polyester, polyurethane, polyethylene, polypropylene, nylon, sintered titanium, deep reactive-ion etched silicon, sintered stainless steel, sintered silica, liquid crystal, glass, borosilicate glass, or mixtures or derivatives thereof.

6. The implantable medical device of claim 1, the barrier layer comprising polyHEMA, agarose, alginates, polyvinyl alcohol, polyacrylate, collagen, PEG, gelatin, or mixtures or derivatives thereof.

7. The implantable medical device of claim 1, further comprising an optical excitation assembly configured to illuminate the sensing element; and an optical detection assembly configured to receive light from the sensing element.

8. The implantable medical device of claim 1, the chemical sensor having a diameter that is greater than 1.0 mm.

9. The implantable medical device of claim 1, the chemical sensor configured to detect an ion selected from the group comprising of potassium, sodium, chloride, calcium, magnesium, lithium, or hydronium.

10. The implantable medical device of claim 1, the structural reinforcing element comprising the shape of a rectangular column, a cylinder, a conical shape, a frustoconical shape, a pyramid, a frustopyramidal shape.

11. The implantable medical device of claim 1, the structural reinforcing element exhibiting rigidity at least 100% greater than the material of the barrier layer.

12. The implantable medical device of claim 1, the structural reinforcing element defining a plurality of apertures therein.

* * * * *